(12) United States Patent
Baseeth et al.

(10) Patent No.: US 12,016,331 B2
(45) Date of Patent: Jun. 25, 2024

(54) MICROEMULSIONS AND USES THEREOF AS DELIVERY SYSTEMS

(71) Applicant: ARCHER DANIELS MIDLAND COMPANY, Decatur, IL (US)

(72) Inventors: Shireen Baseeth, Decatur, IL (US); Swapnil Jadhav, Decatur, IL (US); Bruce Sebree, Oakley, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 0 days.

(21) Appl. No.: 14/382,981

(22) PCT Filed: Mar. 5, 2013

(86) PCT No.: PCT/US2013/029129
§ 371 (c)(1),
(2) Date: Sep. 4, 2014

(87) PCT Pub. No.: WO2013/134267
PCT Pub. Date: Sep. 12, 2013

(65) Prior Publication Data
US 2015/0057157 A1    Feb. 26, 2015

Related U.S. Application Data

(60) Provisional application No. 61/606,771, filed on Mar. 5, 2012.

(51) Int. Cl.
*A01N 25/04* (2006.01)
*A01N 25/30* (2006.01)
*A01N 43/80* (2006.01)

(52) U.S. Cl.
CPC ............. *A01N 25/04* (2013.01); *A01N 25/30* (2013.01); *A01N 43/80* (2013.01)

(58) Field of Classification Search
CPC ......... A01N 25/05; A01N 25/30; A01N 43/80
See application file for complete search history.

(56) References Cited

U.S. PATENT DOCUMENTS

| | | | | |
|---|---|---|---|---|
| 4,056,494 A | * | 11/1977 | Kronstein | C09D 7/63 106/432 |
| 2005/0169951 A1 | * | 8/2005 | Sasson | A01N 25/22 424/405 |
| 2007/0078057 A1 | * | 4/2007 | Rowley | A01N 25/04 504/206 |
| 2008/0194410 A1 | * | 8/2008 | Baseeth | A01N 25/30 504/363 |
| 2010/0173782 A1 | * | 7/2010 | Bohus | B01F 17/0085 504/358 |

* cited by examiner

*Primary Examiner* — Johann R Richter
*Assistant Examiner* — Danielle Johnson
(74) *Attorney, Agent, or Firm* — Andrew F. Nilles

(57) ABSTRACT

Microemulsion compositions include a blend of lecithin and a co-surfactant, and an acidifier. The compositions may further include salts of the acidifier, such as lactic acid or sodium lactate. The microemulsion may be used to produce a multi-functional agricultural adjuvant that is able to deliver an active ingredient such as a pesticide control, pH improve, wetting, and penetration of an agricultural chemical, control droplet size, function at extreme pH or salt concentration and/or other provide another functional benefit.

11 Claims, 10 Drawing Sheets

Left to Right: Prolec L, Prolec G and Li 700

MICROEMULSIONS AND USES THEREOF AS DELIVERY SYSTEMS

CROSS-REFERENCE TO RELATED APPLICATIONS

This application is a national stage entry of International Application No. PCT/US2013/029129, filed Mar. 5, 2013, which itself claims priority to U.S. Provisional Patent Application No. 61/606,771, filed Mar. 5, 2012, each of the contents of the entirety of which are incorporated by this reference.

TECHNICAL FIELD

The present disclosure is directed to compositions comprising lecithin and uses thereof. The invention also relates to methods of using microemulsions to disperse a compound in water. The microemulsions may be bio-based and biodegradable. The present disclosure is also directed to methods for the preparation of such compositions and uses thereof.

BACKGROUND

Anionic phosphate esters are versatile surfactants that exhibit multifunctional properties. The anionic phosphate esters have a phosphate moiety as a head group and are synthesized with phosphoric acid derivatives and alcohol. The synthesis of such phosphate esters typically results in some residual phosphoric acid resulting in a pH as low as two. The anionic phosphate esters are often available in free acid form. The presence of the phosphate group in a formulation for a wetting or dispersing agent enhances the gloss and color acceptance property of a pigment in paint, reduces a viscosity increase due to aging of the paint, improves surface wetting, and provides a stable dispersion.

The presence of the phosphate group of the phosphate esters imparts some interaction with metal surfaces, which exhibits some anti-corrosion and metal adhesion characteristics. Metal cleaning is one area that involves extreme pH conditions as many metal cleaners are alkaline with a pH greater than 10 or acidic with a pH of less than 4. Thus, the surfactants used in metal cleaning must have a good solubility and stability at such extreme pH ranges. In such metal cleaning compositions, low mole ethoxylated phosphate esters and amphoteric surfactants are typically used since such surfactants provide good solubility, stability, wetting, oil/water interfacial reduction, emulsion stabilization, and corrosion protection.

The phosphate esters are also able to solubilize in very high electrolyte solutions such as solutions including sodium silicates. This property is useful in cleaning formulations where the silicate is added to increase the alkalinity and provide corrosion inhibition. Such properties also make the phosphate esters preferred for use in lubrication additives.

Adjuvants are chemically and biologically active compounds that may improve the effectiveness of an herbicide to which they are added. Such adjuvants typically have very specific or limited functionalities in that one adjuvant is used for delivery an active ingredient, one adjuvant is used to control droplet size of a herbicide, one adjuvant is used to control pH, one adjuvant is used to improve wetting, or one adjuvant is used for another specific function. Thus, typically a plurality of adjuvants is needed. The adjuvants may function by either increasing the herbicide's desired impact and/or decreasing the total amount of the herbicide needed to achieve the desired result. Some herbicides require the addition of an adjuvant to be effective. Adjuvants may enhance the penetration of the herbicide into plants by ensuring adequate spray coverage and keeping the herbicide in contact with plant tissues, or may increase the rates of foliar and/or stomatal penetration. Although adjuvants are typically categorized as "inert" or "essentially non-phytotoxic" (i.e. not toxic to plants) compounds, many adjuvants can produce wide ranging effects on physiological and metabolic processes within plants, animals, and/or microorganisms.

The surfactants used in adjuvants may impact the environment not only in their use and disposal, but also in their production and delivery. Agrochemical formulations and delivery systems that include surfactants are evolving to meet the new demands required by their users, producers, and regulatory agencies. Customers are demanding safety, convenience, increased efficiency of application, and more environmentally friendly, sustainable, and green products. The customers want natural, renewable-based products. Pesticide manufacturers and formulators seek improved cost competitiveness and product differentiation. Regulatory bodies across the globe are insisting on the requirement that the adjuvants and/or the surfactants contained therein undergo extensive testing to meet stringent safety criteria. These changing trends in the crop protection adjuvant market are gaining significant importance.

Surfactants based on soybean derivatives can be used to replace petroleum based components. With increased environmental awareness and sustainability efforts, soy based surfactants are being use more since they are also less toxic and biodegradable as compared to their petroleum based counterparts. Also, since lecithin is often food grade, it offers a safety advantage for good agricultural practices.

In addition to making such adjuvants more green and sustainable, multifunctional adjuvants are being developed to make handling and application of an agrochemical easier, while having improved performance. One agrochemical that continually has new adjuvants being developed is glyphosate, where new adjuvants are continually being developed.

One surfactant that is sustainable and green that has been used in adjuvants is lecithin. Commercially available phospholipids/lecithin are mainly by-products from vegetable oil refining. Soy lecithin is a mixture of several phospholipids and is often defined as a mixture of acetone insoluble polar lipids, triglycerides, and other minor components. Lecithin and its components are unique amphiphilic structures having fatty acid chains and a polar head group. Thus, lecithin is known to form bilayers, micelles, or liposomes. Such functionality allows lecithin to be used in foods, cosmetics, pharmaceuticals, and many industrial applications.

A single or isolated phospholipid is seldom used. Typically, a mixture of phospholipids such as commercial crude lecithins or fluid lecithins is used. Fluid lecithin contains neutral lipids such as triacylglycerols and free fatty acids, phospholipids that contain phosphatidylethanolamine (PE), phosphatidyl choline (PC), phosphatidyl inositol (PI), phosphatidic acids (PA), glycolipids, carbohydrates etc. These mixtures of phospholipids offer competitive advantage on the cost and sustainability, as well through performance characteristics, as compared to isolated phospholipids.

The dispersion and emulsion stabilization property of lecithin makes it a good target for encapsulating reactive agents into liposomes. Such liposomes may be used as a vesicular system for increasing the permeation through the skin barrier. The ability of such lecithin liposomes to penetrate skin also makes lecithin useful on a leaf surface as an adjuvant.

While US patent application 2008/0194410, assigned to Archer-Daniels-Midland Company, describes a lecithin based composition that is used as an agricultural adjuvant, needs exist for improved bio-based adjuvants that are multifunctional and exhibit improved properties.

With the growing need for more biobased additives that can replace petroleum based products based on the desire for "greener" products, a need exists for biobased surfactants that can mimic the properties of such phosphate esters and be used in agriculture, drilling, metal working, dispersants, coatings, and latex type products where the biobased products fulfill all the desired characteristics of the petroleum based counterparts.

Lecithin has been considered as a natural ingredient that can form nanodispersions in aqueous mediums and carry high loads of water insoluble actives. However, such aqueous dispersions tend to have limited tolerance to pH and electrolytes.

SUMMARY

In each of its various embodiments, the present invention fulfills these needs. In one embodiment, the compositions of the present invention are bio-based products. In another embodiment, the compositions of the present invention are stable at extreme pH and electrolyte conditions in aqueous systems, without breaking microemulsions formed by such biobased product.

In one embodiment, the microemulsion of the present invention may be used to produce a multifunctional agricultural adjuvant that is able to: deliver an active ingredient such as a pesticide, control pH, improve wetting and penetration of an agricultural chemical, control droplet size, function at extreme pH or salt concentration, and/or other provide another functional benefit. Thus, an agricultural adjuvant produced with a microemulsion of the present invention may alleviate the need to use multiple adjuvants.

In a further embodiment, a microemulsion comprises lecithin; and an acidifier. The acidifier may be selected from the group consisting of an organic acid, a salt of an organic acid, and a combination thereof. The microemulsion may further comprise a co-surfactant. In one embodiment, the acid is the organic acid and the salt of the organic acid. The organic acid may be selected from the group consisting of lactic acid, propionic acid, methyl acetic acid, acetic acid, fumaric acid, citric acid, ascorbic acid, gluconic acid, gluconic delta lactone acid, adipic acid, malic acid, tartaric acid, a hydroxyl acid, salts of any thereof, esters of any thereof, and combinations of any thereof, and in one embodiment, the acidifier is lactic acid. The co-surfactant may have an HLB value of between 4-18 or an HLB value of between 10-18. The lecithin may be selected from the group consisting of crude filtered lecithin, de-oiled lecithin, chemically modified lecithin, enzymatically modified lecithin, standardized lecithin, and combinations of any thereof. The microemulsion may further comprise a solvent having a dielectric constant value of between 2 and 80. The acidifier may be an organic acid. The microemulsion may further comprise a salt of an acid and/or a fatty acid. The microemulsion remains stable at an extreme pH in an aqueous solution and/or remains stable at an extreme electrolyte concentration in an aqueous solution. The microemulsion may have a pH of between 2-12 or between 2-8.

In an additional embodiment, a microemulsion composition may further comprise a compound carried by the microemulsion and/or may comprise water. The microemulsion may further comprise an ester of the organic acid.

In an embodiment, the lecithin may be present in the microemulsion at an amount of between 10-90% by weight and the acidifier may be present at an amount of between 10-90% by weight. In another embodiment, the microemulsion may include lecithin at an amount of between 10-90% by weight, the acidifier at an amount of between 10-90% by weight, and the salt of the acidifier at an amount of between 0.01-60% by weight. In yet a further embodiment, the microemulsion may include the lecithin at an amount of between 5-80% by weight, the acidifier at an amount of between 5-50% by weight, and the co-surfactant at an amount of between 5-50% by weight. In a further embodiment, the microemulsion may include lecithin at an amount of between 5-80% by weight, the acidifier at an amount of between 5-50% by weight, the co-surfactant at an amount of between 5-50% by weight, and the salt of the acid at an amount of between 5-50% by weight.

One embodiment of a process for producing a microemulsion of 1 the present invention comprises mixing lecithin with an acidifier and may further include mixing a salt of an organic acid with the microemulsion.

One method of delivering a compound to a polar solution of the present invention includes mixing the compound with a microemulsion of the present invention and mixing the compound and the microemulsion with the polar solution. The compound may be water insoluble. The compound may be selected from the group consisting of benzimidazoles, dicarboxyimides, quinolulines, (thio)carbamates, benzene sulfamides, carbonic acid amindes, organic (thio)phosphates, pyrethoids, pyraclostrobin, metalaxyl, mefenoxam, trifloxystrobin, imazalil, prochloraz, ipconazole, azoxystrobin, azoles, pyridines, phenylpyrolles, phenoxy, pyrimidines, pyrrolidone, piperazines, moprholines, piperidines, and combinations of any thereof. The acidifier may be lactic acid.

In a further embodiment, a method of delivering a compound to a solution includes mixing the compound with a microemulsion of the present invention and mixing the compound and the microemulsion with the solution. The compound may be selected from the group consisting of salts of 2,4-dichlorophenoxyacetic acid, salts of dicamba, glyphosates (isopropylamine/sodium/potassium salt of glyphosate), salts of acifluorfen, salts of imazaquin, salts of bentazon, salts of imazethapyr, salts of asulam, alcohols, phenols, cresols, heavy metals, salts of heavy metals, and combinations of any thereof. The acidifier may be lactic acid and/or the salt of the organic acid may be sodium lactate.

In a further embodiment, use of the microemulsion of the present invention as an agricultural adjuvant, a drilling additive, a dispersion aid, a grinding aid, a biocide, a wood protection aid, a nanofluid, a nanoreactor, a lubricant, a bioremediation compound, a degreaser, a descaler, a corrosion inhibitor, a textile finishing agent, a drilling fluid, a or a combination thereof is disclosed.

In one embodiment, a method of dispersing a compound in a solution comprises mixing a microemulsion of the present invention with the compound. The compound may be selected from the group consisting of fungicides, herbicides, insecticides, algicides, molluscicides, miticides, rodenticides, nematocides, plant growth regulator, germicides, antibiotics, antibacterials, antivirals, antifungals, antiprotozoals, antiparasites, spermicides, pesticides, antimicrobials, and combinations of any thereof.

In yet a further embodiment, a microemulsion includes a blend of lecithin and a co-surfactant, an acidifier, and a salt of the acidifier. The microemulsion has a pH of between 2-10. The microemulsion may further include a polar solvent such as for example ethyl lactate. The acidifier may be lactic acid and the salt of the acidifier may be sodium lactate.

In another embodiment, a microemulsion comprises lecithin and an acidifier selected from the group consisting of lactic acid, a salt of the lactic acid, and a combination thereof. The microemulsion may be readily soluble in a non-polar solvent.

In another embodiment, a microemulsion comprises a blend of lecithin and a co-surfactant, and an acidifier. The microemulsion may further comprise a salt of the acidifier, and in one embodiment, the microemulsion may have a pH of between 2-10.

In a further embodiment, a process for producing a product includes mixing lecithin with a co-surfactant, thus producing a blend and mixing an acidifier with the blend. In an additional embodiment, a salt of the acidifier may be added to the blend and the acidifier.

In one embodiment, a microemulsion comprises a blend of lecithin and a co-surfactant, an acidifier, and a salt of the acidifier. The microemulsion has a pH of between 2-10.

In other embodiments, uses of the compositions of the present invention as agricultural adjuvants, a drilling additive, a dispersion aid, a grinding aid, a biocide, a wood protection aid, a nanofluid, a lubricant, a bioremediation compound, a degreaser, a descaler, a corrosion inhibitor, a textile finishing agent, a drilling fluid, a or a combination thereof are also disclosed.

It should be understood that this disclosure is not limited to the embodiments disclosed in this Summary, and it is intended to cover modifications that are within the spirit and scope of the invention, as defined by the claims.

BRIEF DESCRIPTION OF THE DRAWINGS

The characteristics and advantages of the present disclosure may be better understood by reference to the accompanying figures, in which.

DETAILED DESCRIPTION

Figure 1:
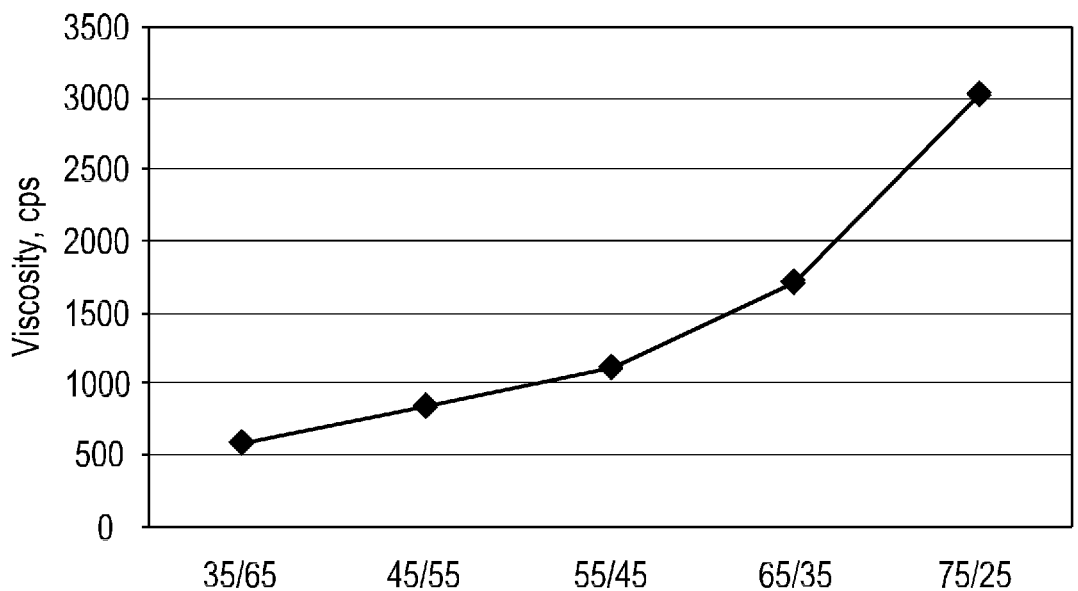
FIG. 1 shows the viscosities of various embodiments of the composition of the present invention.

In the present application, including the claims, other than in the operating examples or where otherwise indicated, all numbers expressing quantities or characteristics are to be understood as being modified in all instances by the term "about". Unless indicated to the contrary, any numerical parameters set forth in the following description may vary depending on the desired properties in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

The embodiments disclosed herein are directed to compositions and methods that are biobased and behave like a synthetic phosphate ester surfactant. The compositions of the present invention are biobased and functional at extreme pH and electrolyte concentrations. In one embodiment, the compositions described herein self-assemble, are thermodynamically stable, and may have a mean particle size of less than one micron.

Lecithin is a lipid substance found in animal and plant tissues such as, for example, egg yolk, soybean, and canola or rapeseed. Lecithin includes various constituents including, but not limited to, phospholipids, such as, for example, phosphatidyl choline ("PC"), phosphatidyl inositol ("PI"), and phosphatidyl ethanolamine ("PE"). The amphiphilic property of lecithin makes it an effective processing aid, emulsifier, dispersant and/or surfactant. Lecithin is also a natural ingredient than can form nanodispersions in aqueous mediums and carry high loads of actives. But, in such aqueous mediums, lecithin tends to have limited tolerance to pH and electrolytes.

Lecithin may be used in applications where modification of the boundary layer between substances is desirable. In the presence of immiscible liquid phase, lecithin can reduce the interfacial surface tension and function as an emulsifier. When used with two or more solid phases, lecithin can function as a lubricant and/or release agent.

In one embodiment, a lecithin based product of the present invention has utility in a dispersant formulation is stable at a low pH, such as down to two, and when used in an aqueous dispersion, the lecithin based product remains stable up to a pH of ten, and also remains stable in high amounts of silicates and electrolytes (up to 40% calcium chloride) without breaking the emulsion. In another embodiment, the composition of the present invention may be used in a drilling fluid with silicate-based fluids where there is a constant challenge for systems that can function at extreme pH.

It has been found that the combination of lecithin and one or more co-surfactants can be used to produce an emulsifier package that mimics a synthetic phosphate ester, is functional at extreme pH, and is functional at extreme electrolyte concentrations. The functionality at extreme pH allows the emulsifier package of the present invention to be used as a descaler, corrosion inhibitor, wetting/dispersing aid in industrial applications such as metal working fluids, lubricants, and textile finish agents. Since the emulsifier package of the present invention functions at extreme pH, calcium, and silicate concentrations, the emulsifier package also finds utility as a water based drilling fluid with minimal environmental impact. The emulsifier package of the present invention may also be used as a delivery vehicle for water soluble and/or water insoluble actives in applications including, without limitation, being used as an agricultural adjuvant. In agricultural systems, the functionality of the emulsifier package makes it useful for spray applications which is desirable since pesticide active ingredients in crop protection need to be uniformly spread in small amounts over a large area, yet not agglomerate in the application process. The emulsifier package of the present invention also has the advantage that a lecithin-cosurfactant blend can be produced, and actives can be added to this lecithin-cosurfactant blend for delivery.

Adjuvants and surfactants are spray solution additives and are considered to be any product added to an agrochemical solution including, but not limited to, biocides, pesticides, herbicides, fungicides, and miticides to improve the performance of a spray solution containing the agrochemical solution. Examples of adjuvants include, but are not limited to, compatibility agents (used to aid mixing two or more herbicides in a common spray solution), drift retardants (used to decrease the potential for herbicide drift), suspension aids (used to aid mixing and suspending herbicide formulations in solution), spray buffers (used to change the spray solution acidity), and surfactants.

The agricultural adjuvants of the present invention provide improved plant cuticle penetration, enhanced wetting and spreading properties, helps reduce spray drift, function as an acidifier, act as a delivery agent for an active ingredient, and helps control the detrimental effects of an alkaline water mix. In an embodiment, water insoluble active ingredients may be dissolved in organic solvents such as mineral oil, methyl esters, lactic acid esters, or others and can be added to the formulation.

Because post emergence herbicide effectiveness is greatly influenced by plant factors such as age, size and the growing conditions of the plant encountered before application, herbicide performance can vary. One way to minimize the variations in post emergence herbicide performance is to use an adjuvant or surfactant in the spray solution. Adjuvants generally improve the effectiveness of post emergence herbicides.

An adjuvant is any additive used in conjunction with a pesticide to increase biological activity and/or to modify various physical properties of a spray solution containing the biocide, fungicide, nematicide, herbicide, pesticide, insecticide or combination of any thereof. Adjuvants and surfactants are added to spray solutions to improve the performance of crop protection compounds (herbicides). Adjuvants also play a key role in controlling the variables including, but not limited to, pesticide stability, solubility, compatibility, penetration, spreading, wetting, coverage, and drift. Surfactants act as an adjuvant that reduces surface tension between the spray solution droplets and the pest target's surface, thus, providing greater coverage.

Surfactants are added to oil adjuvants as emulsifiers to obtain an even distribution of the adjuvant in water. In one embodiment, the adjuvants can affect herbicide performance in many ways such as the spread of spray droplets on the leaf surface, the retention of spray droplets on the leaf, and penetration of the herbicide in the spray droplet through the plant cuticle. Surfactants form a "bridge" between chemicals that don't mix such as, for example, water and oil or water and the wax on a leaf surface. Surfactants lower the surface tension of spray droplets of the herbicide during application and allow for more complete spray coverage and sticking of the herbicide on the plant surface of the droplets. Some herbicides may also contain fatty acids to further improve herbicide retention and penetration. When there are many cations present in the water, as is the case with hard water, the cations including, without limitation, sodium, potassium, calcium, and magnesium can react with the herbicide, thus decreasing the uptake and effectiveness of the herbicide. For instance, a high level of calcium in water (hard water) reduces the control efficacy of glyphosates. Similarly, sodium bicarbonate reduces the efficacy of sethoxydim. A water conditioner, such as ammonium sulfate (which has utility as a nitrogen fertilizer) can negate this effect for glyphosate and sethoxydim. Also, herbicides are generally applied with fertilizers or fertilizer solutions, especially in agricultural settings. Compatibility agents are used to keep these herbicides in suspension. Most herbicides can be applied in nitrogen solutions without any compatibility problems, but compatibility may be poor when water contains high levels of various salts (hard water), or when the water is very cold.

In one embodiment, an adjuvant microemulsion that is based on bio-degradable and bio-renewable ingredients that can be easily mixed with a biological or chemical agent such as a biocide, fungicide, nematacide, herbicide, pesticide or insecticide that is to be dispersed in water prior to application is disclosed. In another embodiment, a method is described for mixing a composition comprising a lecithin-cosurfactant blend and an acidifier, in water, dispersing the composition in water, and applying the dispersed composition to a plant and/or soil.

Also, yet another embodiment of this invention describes a process for producing a microemulsion by mixing lecithin with a surfactant, thus forming a lecithin co-surfactant blend, and mixing an acidifier with the lecithin co-surfactant blend in presence of water, thus forming an adjuvant system. One aspect of this embodiment describes using vegetable fatty acids, soy fatty acids, derivatives of any thereof, and combinations of any thereof as additional components of the adjuvant system.

In one embodiment, a microemulsion comprises a blend of lecithin and a co-surfactant, and an acidifier, where the lecithin is present at 10-90% by weight, the co-surfactant is present at 10-50% by weight, and the acidifier is present at 10-50% by weight. The microemulsion may further comprise a salt of the acidifier which may be present at 10-50% by weight, and in one embodiment, the microemulsion may have a pH of between 2-10.

Also, yet another embodiment of this invention describes a process for producing a microemulsion by mixing lecithin with a surfactant, thus forming a lecithin co-surfactant blend, and mixing an acidifier with the lecithin co-surfactant, thus forming an adjuvant system. One aspect of this embodiment describes using vegetable fatty acids, soy fatty acids, derivatives of any thereof, and combinations of any thereof as additional components of the adjuvant system.

In yet other embodiments, adjuvant systems including microemulsions that may be applied as fertilizer concentrates, in bioremediation applications, in biocide applications and as water conditioning agents are disclosed. One aspect of this embodiment describes the use of bio-based and bio-renewal components for preparing such adjuvant systems.

In one embodiment, the microemulsions of the present invention when used as adjuvants are added to water and thoroughly mixed. A biocide, fungicide, nematacide, herbicide, pesticide or insecticide is added to the water/microemulsion blend and agitated.

Microemulsions are clear, isotropic, thermodynamically stable liquid mixtures including oil, water and a surfactant. The water phase may contain salt(s) and/or other ingredients. Micro emulsions may be prepared from a large number of components. In contrast to ordinary emulsions, micro emulsions form upon simple mixing of the components and do not require high shear conditions. In ternary systems, such as micro emulsions, where two immiscible phases (water and 'oil') are present next to the surfactant phase, the surfactant molecules form a monolayer at the interface between oil and water, with the hydrophobic tails of the surfactant molecules dissolved in the oil phase and the hydrophilic head groups in the aqueous phase. Comparable to the binary systems (water/surfactant or oil/surfactant), self-assembled structures of different morphologies can be obtained ranging from (inverted) spherical and cylindrical micelles to lamellar phases and bi-continuous microemulsions. A water-in-oil microemulsion is an optically transparent mixture including oil, water, and surfactant. Water droplets are in a continuous oil phase stabilized by surfactant.

In one embodiment, an adjuvant system is a microemulsion and may be used as a surfactant to enhance the activity and effectiveness of agricultural chemicals, such as herbicides, defoliants, desiccants, plant growth regulators, insecticides, fungicides, foliar nutrients, acaracides, and combinations of any thereof. The adjuvant system provides more uniform coverage by decreasing surface tension of spray solutions, thus, aiding in penetration. The adjuvant system may also be used as an acidifying agent to lower pH of spraying solutions, thus, preventing alkaline hydrolysis of pesticides sensitive to high pH.

In other embodiments, the secondary ingredients may be dissolved in water. Generally, the microemulsion adjuvant compositions are provided separately and a penetrant (such as a co-surfactant) is combined when used. The final compositions may be diluted in water and sprayed or poured onto the soil. In one embodiment, ingredients may be present in one phase for ease of use and are ready to deliver to the soil by diluting with water. In one embodiment, concentrations of the first ingredient in the aqueous solution may range from 0.1 to 20 percent. It will be apparent by those of ordinary skill in the art that the percentages and methods used for application will vary with the type of crop, type of control desired, and/or other conditions and may be optimized using routine experimentation. The co-surfactants used may also include without limitation, for example, polyoxyethylene derivatives of sorbitan monoester, such as a polyethylene oxide of sorbitan fatty acid esters (e.g., sorbitan monopalmitate, sorbitan monooleate, sorbitan monostearate). These compounds are available under the trade name of "TWEEN" of Uniqema Company (a Delaware Corporation) such as TWEEN 60 or TWEEN 80. Any other suitable surfactant in the desired HLB range may be used. Such surfactants are available from numerous suppliers such as, for example, BASF (Florham Park, NJ), Lonza (Allendale, NJ), Stepan (Northfield, IL), Kerry (Beloit, WI).

Another embodiment of the invention enables the use of hard (e.g., well) water for applying an herbicide to soil. Dispersibility of the composition of the present invention in hard water is important because of the cost associated with treating water to reduce its hardness. Well water high in mineral (e.g., calcium, magnesium and iron) content may also be used. The adjuvant system described herein, upon mixing with the herbicide may be used at rates such as from about 6 pounds per acre to about 300 pounds per acre upon dilution in water. In certain embodiments, the adjuvant system may be used at rates of one pound per acre or less depending upon the amount necessary to attain effective control by any application technique in which the adjuvant system and biocides are brought in mutual contact, such as to the foliage of the plant or grass, to the soil itself, or other plant pest desired to be controlled.

In another embodiment, the compositions of the present invention may be used in conjunction with various fertilizers.

The teachings of this invention may also be used in conjunction with any biological or chemical agent including, but not limited to, a biocide, fungicide, nematacide, herbicide, pesticide, insecticide or combination of any thereof that may be dispersed in water prior to application. For instance, substances used in crop protection which may be dispersed in water prior to application may be developed by the teachings of this invention. A blend of lecithin and a co-surfactant may be prepared and blended with the biological or chemical agent that is required for application to produce a stable dispersion in water. In one embodiment, the dispersion may also be dispersed in hard water.

In another embodiment, the emulsifier package may be used to solubilize essential oils or any water soluble active in the form of a water phase. In one embodiment, the emulsifier package of the present invention can be used as a delivery system to load as high as about 35% oil or about 18% water, yet still be clear and stable.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin. Lecithins useful in the disclosed compositions and methods may comprise co-emulsifiers having a hydrophilic-lipophilic balance value ranging from 10.0 to 24.0, and in certain embodiments 10.0 to 18.0.

The emulsifier and/or surfactant properties of an amphiphilic substance such as lecithin, for example, may be predicted at least in part by the hydrophilic-lipophilic balance ("HLB") value of the substance. The HLB value may function as an index of the relative preference of an amphiphilic substance for oil or water—the higher the HLB value, the more hydrophilic the molecule; the lower the HLB value, the more hydrophobic the molecule. A description of HLB values is provided in U.S. Pat. No. 6,677,327, which is incorporated by reference herein in its entirety. HLB is also described in Griffin, "Classification of Surface-Active Agents by 'HLB,'" *J Soc. Cosmetic Chemists* 1 (1949); Griffin, "Calculation of HLB Values of Non-Ionic Surfactants," *J Soc. Cosmetic Chemists* 5 (1954); Davies, "A quantitative kinetic theory of emulsion type, I. Physical chemistry of the emulsifying agent," *Gas/Liquid and Liquid/Liquid Interfaces, Proceedings of the 2d International Congress on Surface Activity* (1957); and Schick, "Nonionic Surfactants: Physical Chemistry", Marcel Dekker, Inc., New York, N.Y., pp. 439-47 (1987), each of which is incorporated by reference herein in its entirety.

In various embodiments, the acidifier used in the disclosed compositions and methods may be selected from the group of acidifiers consisting of a lactic acid, propionic acid, methyl acetic acid, acetic acid, fumaric acid, citric acid, ascorbic acid, gluconic acid, gluconic delta lactone acid, adipic acid, malic acid, tartaric acid, a hydroxy acid, salts of any thereof, esters of any thereof, or combinations of any thereof. In another embodiment, the acidifier is selected from lactic acid, sodium lactate, ethyl lactate, or combinations of any thereof. The acidifier may also be a bio-derived acid, an organic acid, or a combination thereof. In another embodiment, a pH of the composition may be below 6, below 5, or below 4.

Substances of a bio-derived origin are derived from biological materials as opposed to being derived from petrochemical sources. Bio-derived substances may be differentiated from petroleum derived substances by their carbon isotope ratios using ASTM International Radioisotope Standard Method D 6866. As used herein, the term "bio-derived" refers to being derived from or synthesized by a renewable biological feedstock, such as, for example, an agricultural, forestry, plant, fungal, bacterial, or animal feedstock.

Various agencies have established certification requirements for determining bio-derived content. These methods require the measurement of variations in isotopic abundance between bio-derived products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-derived products compared to petroleum products. Bio-derived content of a product may be verified by ASTM International Radioisotope Standard Method D 6866. ASTM International Radioisotope Standard Method D 6866 determines bio-derived content of a material based on the amount of bio-derived carbon in the material or product as a percent of the weight (mass) of the total organic carbon in the material or product. Bio-derived products will have a carbon isotope ratio characteristic of a biologically derived composition.

Bio-derived materials offer an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. In most instances, bio-derived chemicals and products formed therefrom are less burdensome on the environment than petrochemicals and products formed from petrochemicals. As the supply of easily extracted petrochemicals continues to be depleted, the economics of petrochemical production will likely force the cost of the petrochemicals and petroleum derived products to be higher compared to bio-based products. In addition, companies may benefit from the marketing advantages associated with bio-derived products from renewable resources in the view of a public becoming more concerned with the supply of petrochemicals.

In various embodiments, the disclosed compositions may also comprise one or more co-surfactants. The one or more co-surfactants may comprise one or more anionic surfactants, one or more non-ionic surfactants, or combinations of one or more anionic surfactants and one or more non-ionic surfactants. In various embodiments, the co-surfactant or co-surfactant combinations may have a hydrophilic-lipophilic balance ranging from 10.0 to 24.0, and in some embodiments from 10.0 to 18.0. In another embodiment, co-surfactants which have HLB value of 12 to 16 may be used. The surfactant blend may be produced by mixing lecithin, such as for example fluidized lecithin, crude lecithin, de-oiled lecithin or any combination thereof, with a composition containing the surfactants and co-solvents. In one embodiment, the range of such blends may comprise lecithin in a concentration of between about 50 percent by weight to about 90 percent by weight with the remainder of the blend comprising a co-surfactant.

The co-surfactant used may also contain propylene glycol, ethylene glycol, glycerol, short chain fatty acids, esters or any combinations thereof.

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof. In various embodiments, the surfactant comprises an anionic surfactant, such as, for example, a phosphate ester.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof. In various embodiments, the surfactant comprises a non-ionic surfactant, such as, for example, a fatty acid ethoxylate.

In another embodiment, the compositions of the present invention may be food grade and include a food grade surfactant such as, for example, a polysorbate. In one embodiment, the microemulsion of the present invention useful in food applications where lecithin needs to be compatible with an acidic pH.

The embodiments disclosed herein are also directed to methods or processes of preparing the disclosed compositions. In various embodiments, lecithin is mixed with a cosurfactant at ambient temperature and constantly stirred for a period of time. In another embodiment, an acidifier is added to the lecithin/co-surfactant blend at ambient temperature and mixed for a period of time. In another embodiment, water may be added after the acidifier is mixed with the lecithin/co-surfactant blend.

The embodiments disclosed herein are also directed to methods of using the disclosed compositions. In various embodiments, the disclosed compositions are used to aid in the dispersion or wetting of an ingredient in a formulation such as, for example, concrete, ceramic, fiberglass, plastic, ink, paint, or other coating. The disclosed compositions are mixed into the formulation to disperse or wet at least one ingredient, such as, for example, a pigment. In various embodiments, the disclosed compositions comprise low-VOC bio-derived additives for use in a variety of formulations.

As described herein, the disclosed compositions are suitable for formulating solvent and water based paints, inks, and other coating systems. The amphiphilic properties of the disclosed compositions allows for their use as good wetting and stabilizing agents for organic pigments, inorganic pigments, carbon black, or titanium dioxide. The disclosed compositions are also suitable for a wide variety of pigment concentrates. In various embodiments, as illustrated herein, the disclosed compositions are added as a grinding aid in pigment dispersion processes during formulation of paints, inks and other coating systems.

In various embodiments, as illustrated herein, the disclosed compositions may function as low-VOC dispersants exhibiting low-grind viscosity, high pigment load, low foam, high color development, and fast dispersion/wetting. In various embodiments, the disclosed compositions may comprise an emulsifier blend free of alkyl phenol ethoxylates.

EXAMPLES

The following exemplary, non-limiting examples are provided to further describe the embodiments presented herein. Those having ordinary skill in the art will appreciate that variations of these Examples are possible within the scope of the invention.

Example 1

This example describes a method of making a lecithin concentrate that is water dispersible. A lecithin-cosurfactant blend was prepared by mixing: YELKIN T brand lecithin (available from Archer-Daniels-Midland Company of, Decatur, IL) in an amount of 73 percent by weight; a co-surfactant, NINEX MT-610 brand fatty acid ethoxylate (available from Stepan, Northfield, IL) in an amount of 20 percent by weight; and fatty acids an amount of 7 percent by weight. The components were mixed at 50° C. under constant stirring for between 30 minutes to 60 minutes, thus producing an amber, transparent lecithin concentrate. The lecithin concentrate is hydrophilic and easily dispersible in water, particularly when the HLB is around 10-12. In addition to the fatty acid ethoxylate, other co-surfactants having an HLB of between 10-18 would function as well.

Example 2

Lactic acid of three different strengths, 80%, 85%, or 88%, was added to the lecithin concentrate in the amounts recited in Table 1. The concentration of the lactic acid ranged from 80-88% by weight.

TABLE 1

| Sample | Lecithin Concentrate (%) | Lactic Acid (%) |
| --- | --- | --- |
| 1 | 35 | 65 |
| 2 | 45 | 55 |
| 3 | 55 | 45 |
| 4 | 65 | 35 |
| 5 | 75 | 25 |

Each of the blends of the lecithin concentrate and lactic acid of Table 1 were completely clear and transparent without any flocculation. The lactic acid was infinitely soluble in the lecithin concentrate. The viscosity of the blends of Table 1 at 25° C. and 30 rpm are shown in FIG. 1.

Example 3

In another embodiment, 41% by weight of the lecithin concentrate of Example 1 is mixed with 32% by weight of 88% strength lactic acid, 13.5% by weight of ethyl lactate, and 13.5% by weight water. The components were mixed at room temperature with constant stirring for 30 minutes to obtain a clear composition that easily forms a stable, milky dispersion in water. The pH of this composition is 2.

The order that the components are added is important for a couple of reasons. First, since the lecithin concentrate has a high HLB value, placing the lecithin concentrate in contact with water hydrates the lecithin concentrate where the lecithin concentrate emulsifies. Once this emulsification occurs, it cannot be reversed. Second, the lecithin concentrate changes in structural conformation when an acidifier is added before water. By adding the acidifier before the water, a unique molecular structure is created and this structure binds water in a way that results in a clear solution, where the water is present as nano droplets inside a micelle. By adding the acidifier before the water, no emulsification occurs and good compartmentalization of oil and water occurs.

Example 4

58% by weight of the lecithin-co-surfactant blend of Example 2 was mixed with 22% by weight of 60% strength sodium lactate (available from Archer-Daniels-Midland Company, Decatur, IL), followed by adding 9% by weight of 88% strength lactic acid (available from Archer-Daniels-Midland Company, Decatur, IL). To this blend, 4% by weight of ethyl lactate (available from Archer-Daniels-Midland Company, Decatur, IL), followed by 7% by weight of water was added, followed by constant stirring at room temperature for 30 minutes to produce a clear composition having a pH of 4.5, where the composition easily forms a stable, milky dispersion in water.

Example 5

56% by weight of the lecithin-co-surfactant blend of Example 2 was mixed with 22% by weight of 60% strength sodium lactate (available from Archer-Daniels-Midland Company, Decatur, IL), followed by adding 9% by weight of 88% strength lactic acid (available from Archer-Daniels-Midland Company, Decatur, IL). To this blend, 4% by weight ethyl lactate (available from Archer-Daniels-Midland Company, Decatur, IL) was added, followed by 9% by weight propylene glycol (available from Archer-Daniels-Midland Company, Decatur, IL), and the composition was constantly stirred for thirty minutes to obtain a clear composition that easily forms a stable milky dispersion in water. This composition had a pH of 4.5, a very low viscosity, and pour point.

Traditional lecithin products are usually very viscous at low temperatures. In applications of such traditional lecithin products when there is a demand for low pour point products, the emulsifier would typically be diluted in a solvent, although such applications do not offer the same water dispersibility. In the present invention, a composition that has almost 20% moisture in the product results in low pour point property. A good example of practicing green chemistry is designing chemicals that are more benign to the environment, not just in the process, but also at the end user application.

Example 6

A lecithin-cosurfactant blend was prepared by mixing 72% by weight lecithin (available from Archer-Daniels-Midland Company, Decatur, IL), 20% by weight polysorbate 80 (available from BASF, New Jersey), and 7% by weight soy fatty acids. The lecithin, polysorbate 80, and soy fatty acids were mixed at 50° C. under constant stirring for between 30-60 minutes to produce an amber, transparent, lecithin-cosurfactant blend.

Example 7

58% by weight of the lecithin-cosurfactant blend of Example 2 was mixed with 22% by weight of 60% strength sodium lactate (available from Archer-Daniels-Midland Company, Decatur, IL), followed by 9% by weight of 88% strength lactic acid (available from Archer-Daniels-Midland Company, Decatur, IL). To this blend, 4% by weight ethyl lactate (available from Archer-Daniels-Midland Company, Decatur, IL) was added followed by 7% by weight of water. The ingredients were constantly stirred for about thirty minutes at room temperature to obtain a clear system that easily forms a stable, milky dispersion in water. The pH of this blend was about 4.5.

In another embodiment, a complete food grade version of this composition may be made as the co-surfactant used in this Example is considered an inert ingredient under current U.S. Regulations and are exempt from limits of tolerance according to the United States Environmental Protection Agency.

The composition of this Example was diluted in a variety of polar and non-polar solvents including water, glycerol, propylene glycol, soy methyl ester, ethyl lactate, and their blends. By diluting the composition in the solvents, active ingredients can be added and used in various formulations. Such versatility enables the composition of the present invention to function as a delivery system across a multitude of applications.

Example 8

58% by weight of the lecithin-cosurfactant blend of Example 2 was mixed with 22% by weight of 60% strength sodium lactate (available from Archer-Daniels-Midland Company, Decatur, IL), followed by adding 9% by weight of 88% strength lactic acid (available from Archer-Daniels-Midland Company, Decatur, IL). 4% by weight ethyl lactate (available from Archer-Daniels-Midland Company, Decatur, IL) was added to this blend and constantly stirred at room temperature for about 30 minutes to obtain a clear system that easily forms a stable, milky dispersion in water. The pH of this blend was about 4.5. Once this product is made, water soluble herbicides, fungicides, or other material can be added to the product and subsequently dispersed in water.

Example 9

58% by weight of the lecithin-cosurfactant blend of Example 2 was mixed with 22% by weight of 60% strength sodium lactate (available from Archer-Daniels-Midland Company, Decatur, IL), followed by adding 9% by weight of 88% strength lactic acid (available from Archer-Daniels-Midland Company, Decatur, IL). 4% by weight ethyl lactate (available from Archer-Daniels-Midland Company, Decatur, IL) was added to this blend, followed by adding 7% by weight of a 5% (w/v) lysine, betaine, or 33% concentration of an ammonium sulfate solution. The ingredients were constantly stirred at room temperature for about 30 minutes to obtain a clear system that easily forms a stable milky dispersion in water. The pH of this blend was about 4.5.

Example 10

58% by weight of the lecithin-cosurfactant blend of Example 2 was mixed with 22% by weight of 60% strength sodium lactate (available from Archer-Daniels-Midland Company, Decatur, IL), followed by adding 9% by weight of 88% strength lactic acid (available from Archer-Daniels-Midland Company, Decatur, IL). 4% by weight ethyl lactate (available from Archer-Daniels-Midland Company, Decatur, IL) was added to this blend, followed by the addition of 7% by weight of a sea water substitute solution (prepared according to ASTM Standard Designation: D1141-98 (Re-approved 2003)). The ingredients were constantly stirred at room temperature for about 30 minutes to obtain a clear system that easily forms a stable milky dispersion in water. The pH of this blend was about 4.5. This Example shows that the electrolyte compositions does not affect the self assembly of the emulsifier package of the present invention.

Example 11

The product of Example 3 was tested for electrolyte compatibility. The pH of this product was about 2. The stability of the product of Example 3 was subjected to: a pH of about 10 using sodium hydroxide, a 10% sodium silicate solution, and 40% calcium chloride. The blend of Example 3 was compared side by side with 2 phosphate esters, Stepfac 8170 (an ethoxylated APE type phosphate ester available from Stepan, Northfield, IL) and Surfonic PE-BP2 (an APE free type phosphate ester available from Huntsman Chemical, Texas). The results are shown in Table 2. This example shows that the product of the present invention can remain dispersible at extreme pH and electrolyte conditions, functioning even better than the phosphate ester surfactants.

TABLE 2

| Product | Dispersibility in 10% sodium silicate | Dispersibility in 40% calcium chloride | Dispersibility at pH of 10 |
| --- | --- | --- | --- |
| Example 3 product | YES | YES | YES |
| Stepfac 8170 | YES | NO | YES |
| Surfonic PE-BP2 | YES | NO | NO |

This Example illustrates that the unique composition of the present invention is able to increase the rate of penetration by reducing the torque and drag, even in the presence of high levels of silicates and calcium. Thus, the compositions of the present invention can replace traditional phosphate ester surfactants used in water based drilling additives.

Example 12

The product from Example 8 can be used to make a degreaser formulation that can be made with a food grade emulsifier. Soy methyl ester and ethyl lactate blends of 70:30 are known for having utility in degreasing and lubricating applications. The product from Example 8 is blended with the 70:30 blend of soy methyl ester/ethyl lactate blend at any ratio depending on the desired use, thus producing a degreasing formulation. Since the product from Example 8 is also compatible at higher pH and electrolyte concentration, it can also be used in metal working fluids and as corrosion inhibitors.

Example 13

The composition of Example 4 or Example 8 is diluted with an herbicide in water, optionally hard water, to form an emulsion comprising between 0.1-1.0% by weight of the composition/herbicide blend in water. The emulsion may be applied in the amount of 0.1-1.0 gallons per acre of land, depending upon the herbicide control desired.

Example 14

The lecithin-cosurfactant blend from Example 6 was mixed in an amount of 62 percent by weight with sodium lactate of 60% strength (available from Archer Daniels Midland Company of, Decatur, IL) in an amount of 23 percent by weight, followed by 10% lactic acid of 88% strength (available from Archer Daniels Midland Company of, Decatur, IL).

To this blend Ethyl lactate (available from Archer Daniels Midland Company of, Decatur, IL) in an amount of 4 percent by weight at room temperature with constant stirring for thirty minutes to obtain a clear system that easily forms a stable milky dispersion in water. The pH of this blend is at 4.5. This product is food grade alternative of the technology using acidifier such as lactic acid.

Example 15

The product from Example 14 at 80 weight percent was diluted with 20 weight percent of food grade mineral oil. The viscosity of this blend drops five folds from 40,000 cps to 8000 cps measured using Brookfield viscometer at 30 rpm at 25° C. The final product is very water dispersible with a pH of 4.5. This product can be used as a food grade biolubricant with biocidal properties coming from low pH lactic acid. The product is very heat resistant unlike a typical lecithin that breakdown with darkening at 160° F.

Example 16

The product from Example 14 at 80 weight percent was diluted with 4 weight percent of Ethyl lactate. This blend allows the addition of active ingredients even if they are diluted in water. MCMI (methyl chloro methyl isothiazolone) and DCOI (4,5-dichloro-2-n-octyl-4-isothiazolin-3-one) has broad spectrum efficacy versus bacteria, algae, and fungi. These chemicals can be loaded at a 16 weight percent to the above. Increased loading of the actives is possible with subtle variation of the lecithin concentrate to ethyl lactate weight ratio. The final product is very water dispersible with a pH of 4.5. This product can be used as a microbial control in industrial waste water applications.

Example 17

Different ratios of Yelkin SS brand lecithin (available from Archer Daniels Midland Company of, Decatur, IL) and lactic acid of 88% strength (available from Archer Daniels Midland Company of, Decatur, IL) were blended at room temperature with constant stirring for thirty minutes to obtain a clear system. This was readily soluble in a non-polar solvent such as mineral oil, medium chain triglycerides, or vegetable oils. This allows the addition of lactic acid to the fat phase of a food system to offer antimicrobial properties when fat is associated with moisture. The solubility in oil in shown in Table 3. The solubility in oils show that these blends are low HLB systems.

TABLE 3

| Yelkin SS | 88% Lactic acid | Solubility | Stability |
|---|---|---|---|
| 90 | 10 | Soluble | Clear |
| 80 | 20 | Soluble | Clear |
| 70 | 30 | Soluble | Clear |
| 60 | 40 | Soluble | Clear |
| 50 | 50 | Soluble | Clear |

Example 18

Different ratios of lecithin Yelkin SS (available from Archer Daniels Midland Company of, Decatur, IL) and lactic acid of 88% strength (available from Archer Daniels Midland Company of, Decatur, IL) were blended at room temperature with constant stirring for thirty minutes to obtain a clear system. The pH of this blend will be very low. However, the pH can be modified to relatively a level that an enzyme such as protease or α- or β-amylase can be active by addition of sodium lactate. This can be a good enzyme delivery system in all baking applications.

Example 19

The composition of Example 4 or Example 8 is diluted with an herbicide in water, optionally hard water, to form an emulsion comprising between 0.1-10% by weight of the composition and may be used as a good mold inhibitor for wood protection systems. Also, optionally lemon oil, pine oil, methyl esters, or combinations thereof may be added in the composition for degreasing the surface to remove the mold on the wood surface.

Example 20

The acidifier properties of the composition of Example 4 and Example 8 were tested for acidifier functionality as an adjuvant. The compositions were compared to a commercial acidifier adjuvant containing propionic acid. The lactic containing compositions of the present invention have the advantage of being less corrosive and volatile as compared to compositions including propionic acid, and also increased the biobased content of the acidifier adjuvant to about 95%.

Figure 2:
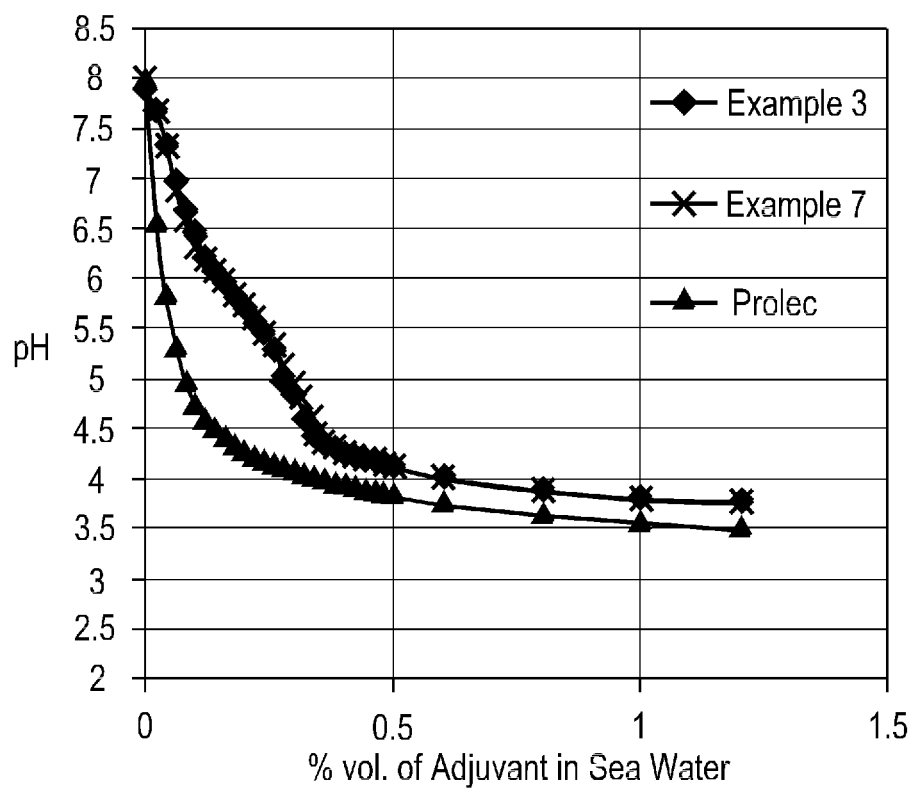
FIG. 2 shows the pH of various embodiments of the composition of the present invention when diluted in a sea water substitute.

The adjuvant blends from Example 4, Example 8, and PROLEC brand agricultural adjuvant were titrated with a sea water substitute (pH of 8, prepared according to ASTM Standard Designation: D1141-98 (Reapproved 2003)) containing as much as 1200 ppm of calcium salt along with other metal ions. The pH of the adjuvant blends and sea water substitute are shown in FIG. 2. In addition to the acidifier property, the compositions of the present invention have other advantages such as being able to accommodate actives that are readily degradable in water, accommodating actives that are poorly delivered in a cuticular layer in a system that has a protecting effect, and being hard water tolerant.

Example 21

Figure 3:
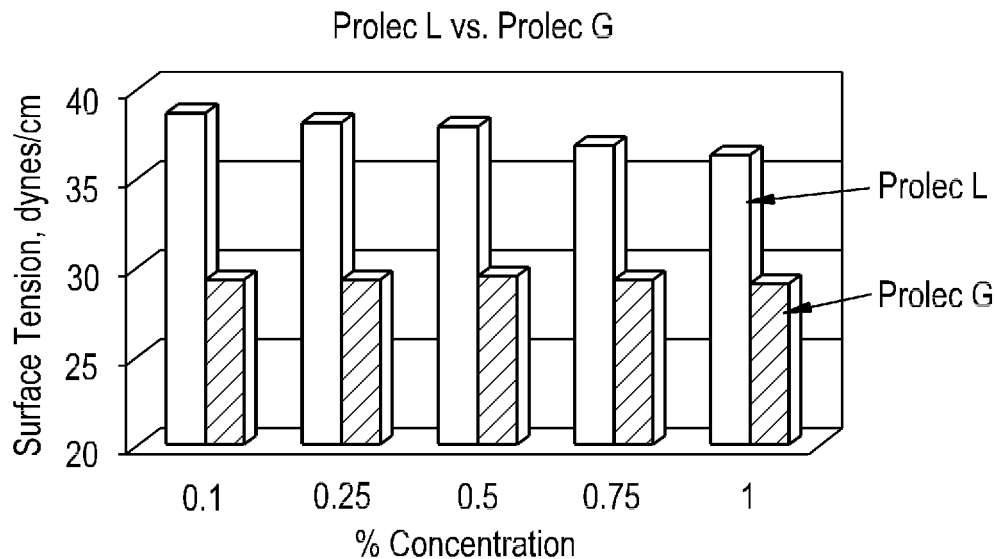
FIG. 3 shows the surface tension of various embodiments of the composition of the present invention.
Figure 4:
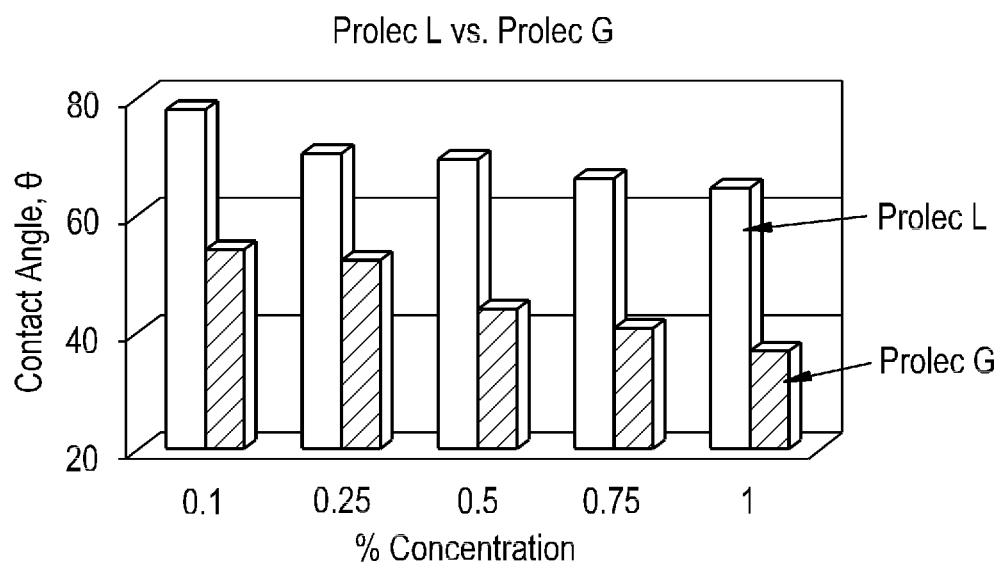
FIG. 4 shows the contact angle of various embodiments of the composition of the present invention.
Figure 5:
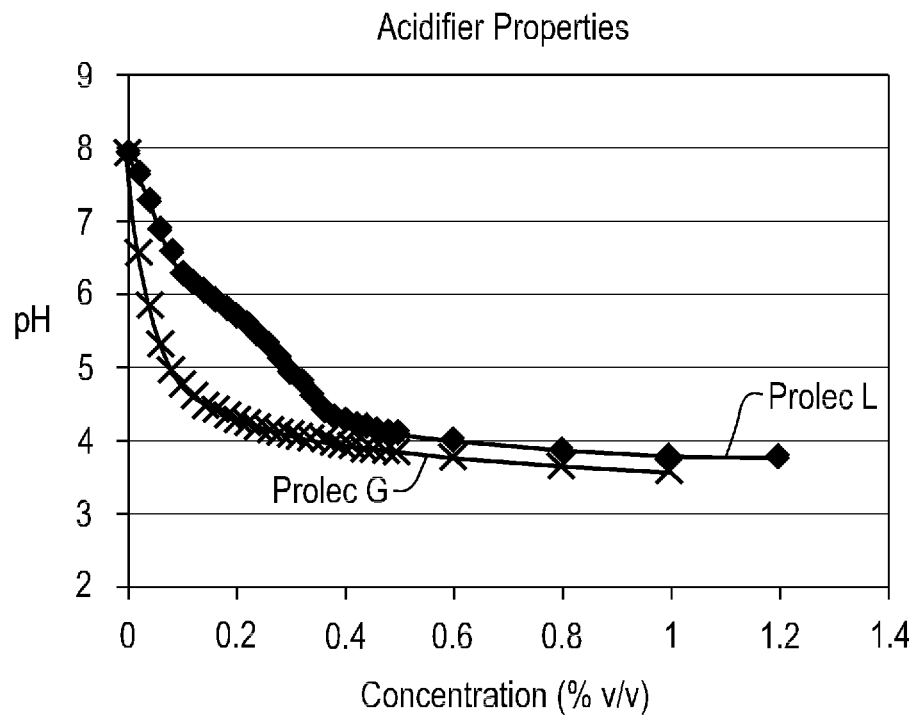
FIG. 5 shows the pH of various embodiments of the composition of the present invention when diluted.
Figure 6:
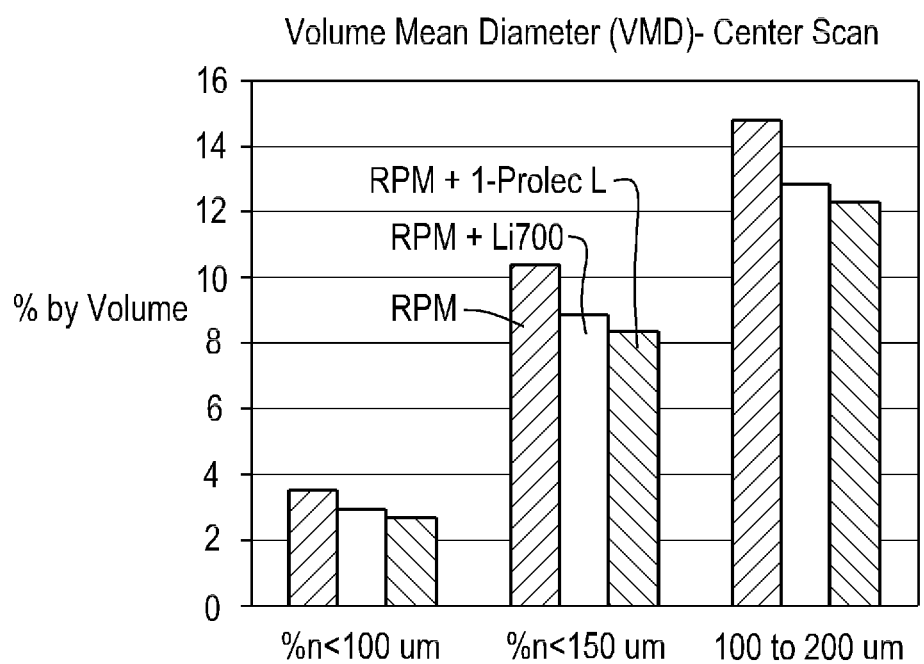
FIG. 6 shows the volume mean diameter of droplets of an agricultural adjuvant produced with one embodiment of a microemulsion of the present invention.
Figure 7:
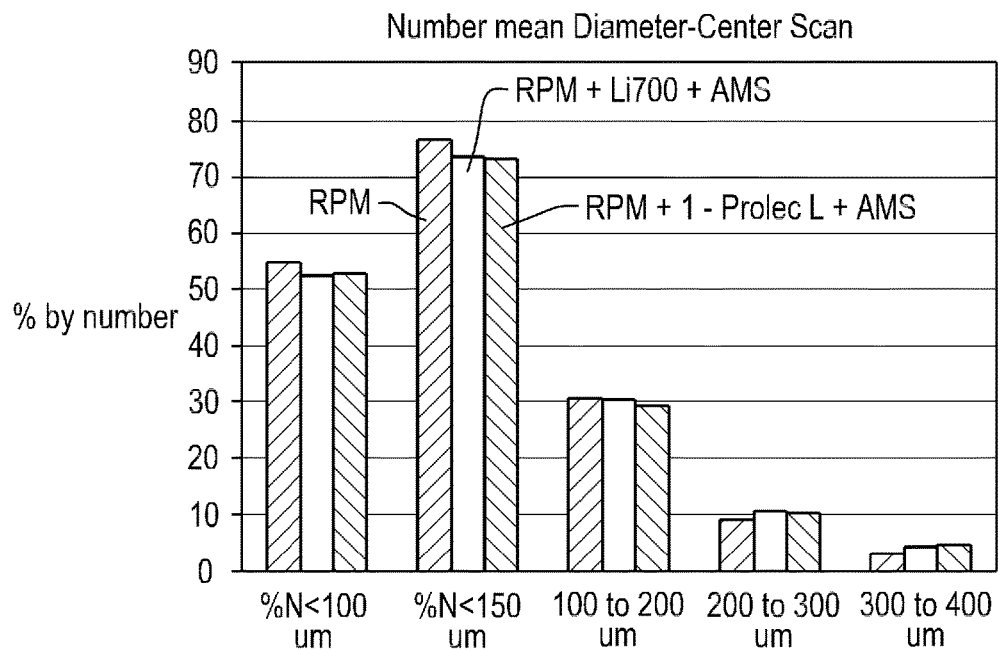
FIG. 7 shows the number mean diameter of droplets of an agricultural adjuvant produced with one embodiment of a microemulsion of the present invention.
Figure 8:
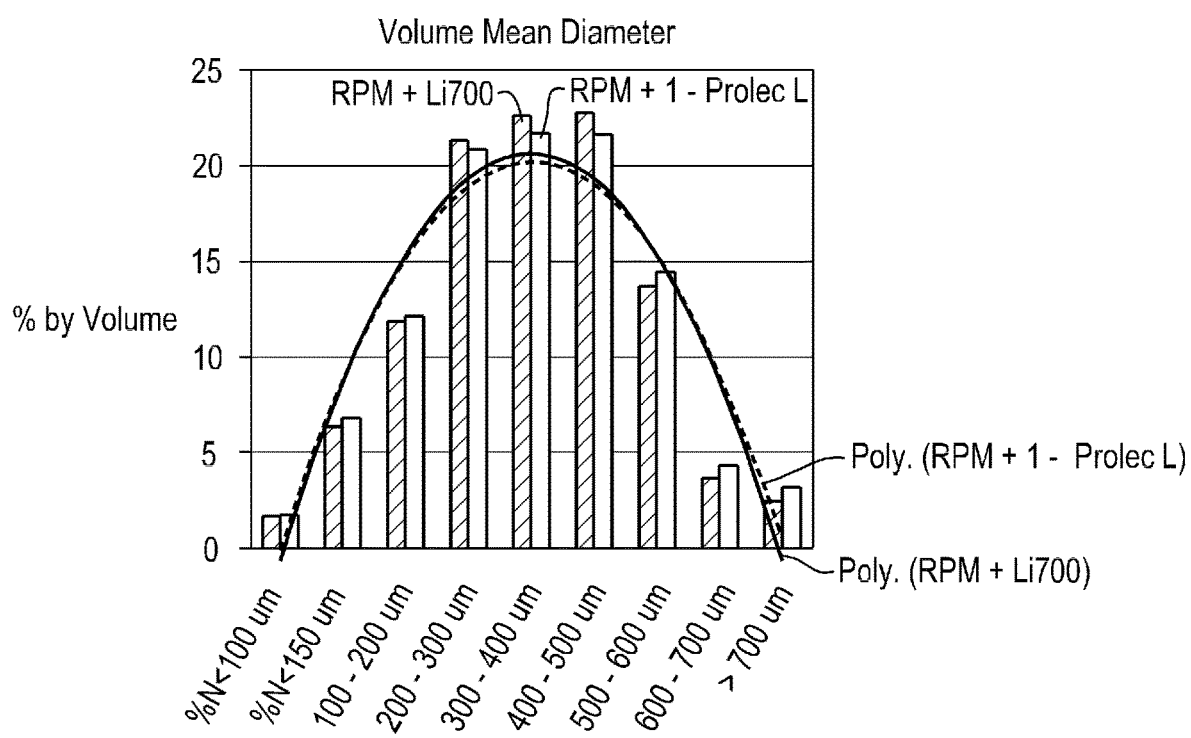
FIG. 8 shows the volume mean diameter of droplets of an agricultural adjuvant produced with one embodiment of a microemulsion of the present invention.
Figure 9:
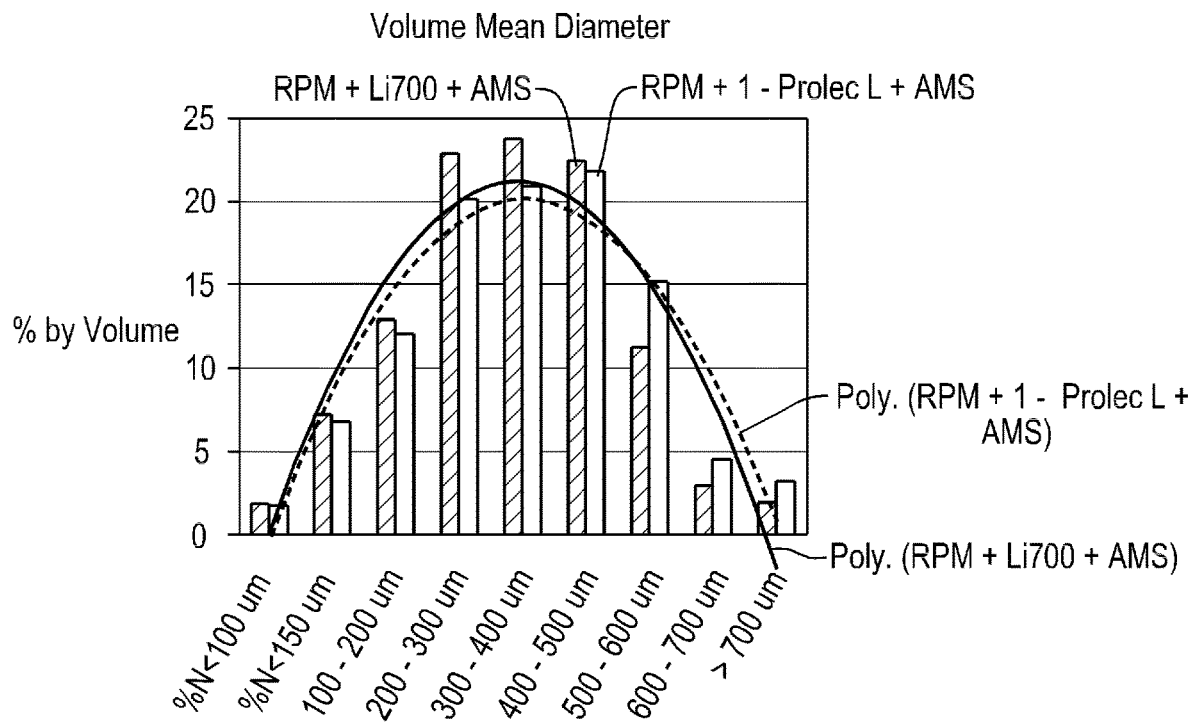
FIG. 9 shows the volume mean diameter of droplets of an agricultural adjuvant produced with one embodiment of a microemulsion of the present invention.
Figure 10:
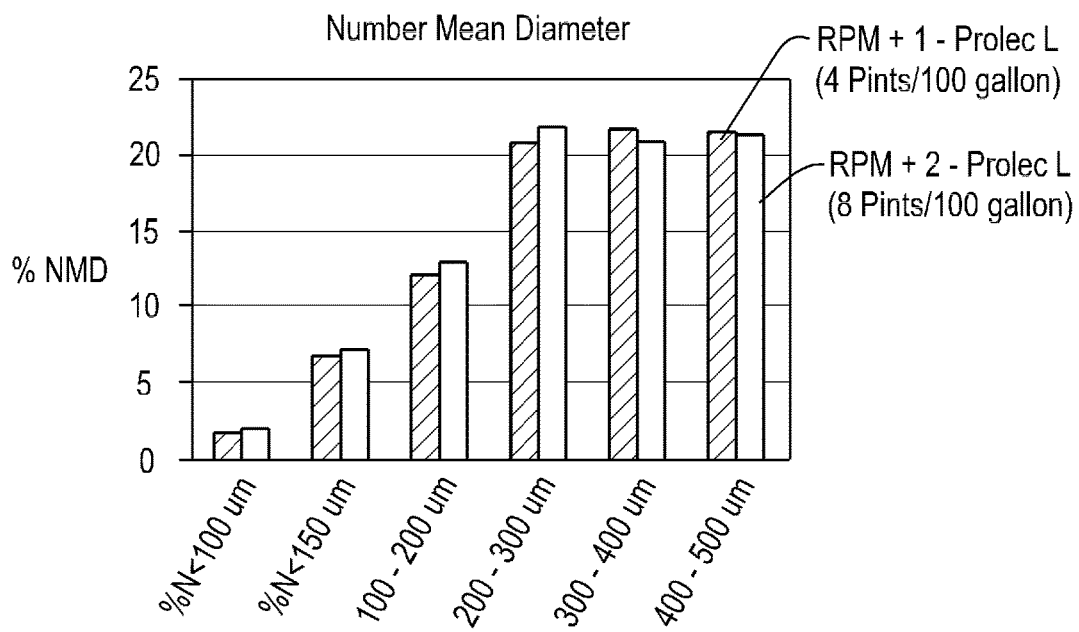
FIG. 10 shows the number mean diameter of droplets of an agricultural adjuvant produced with one embodiment of a microemulsion of the present invention.
Figure 11:
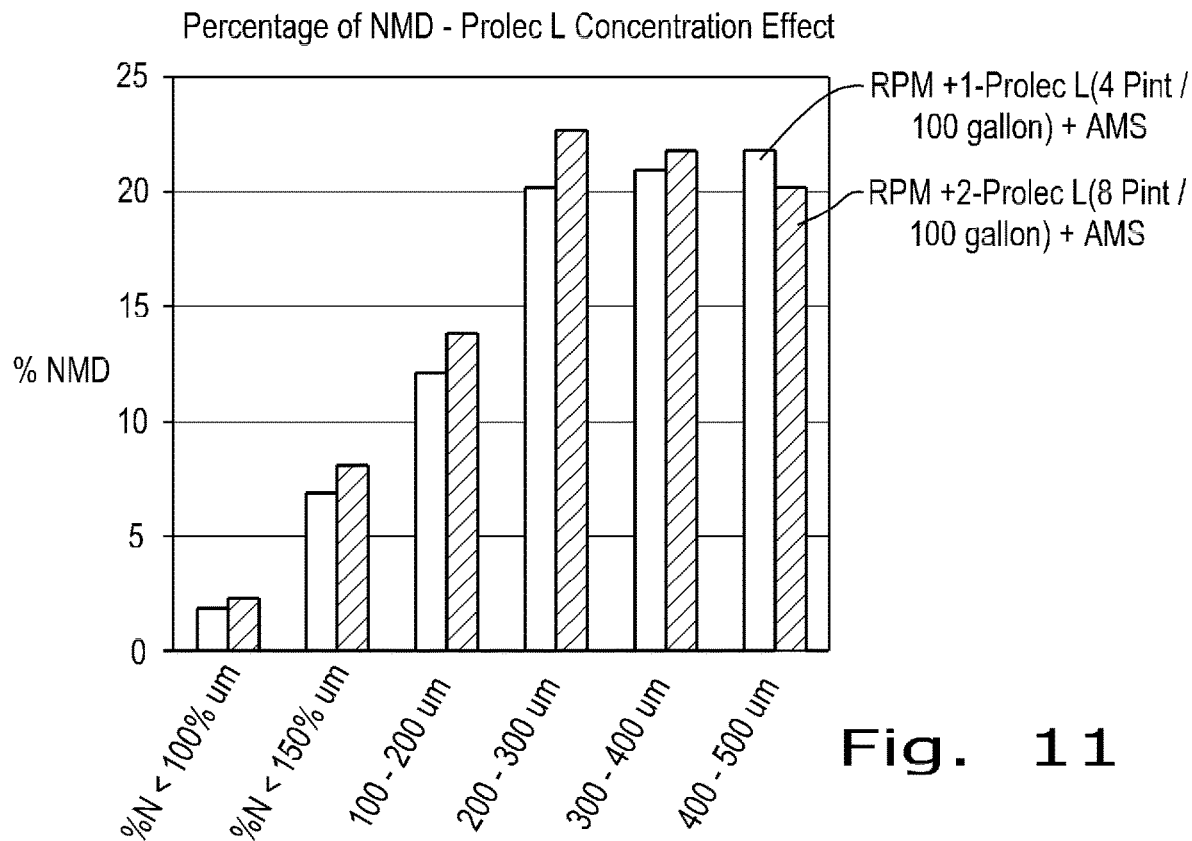
FIG. 11 shows the percentage of number mean diameter of droplets of an agricultural adjuvant produced with one embodiment of a microemulsion of the present invention.
Figure 12:
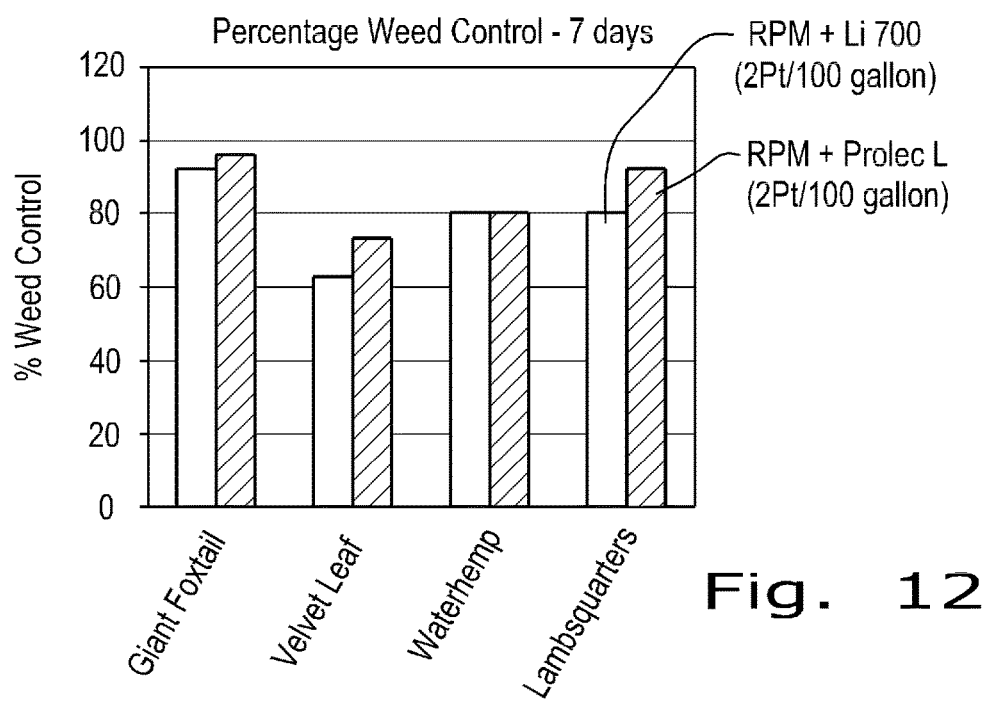
FIG. 12 shows percentage weed control at 7 days of an agricultural adjuvant produced with one embodiment of a microemulsion of the present invention.
Figure 13:
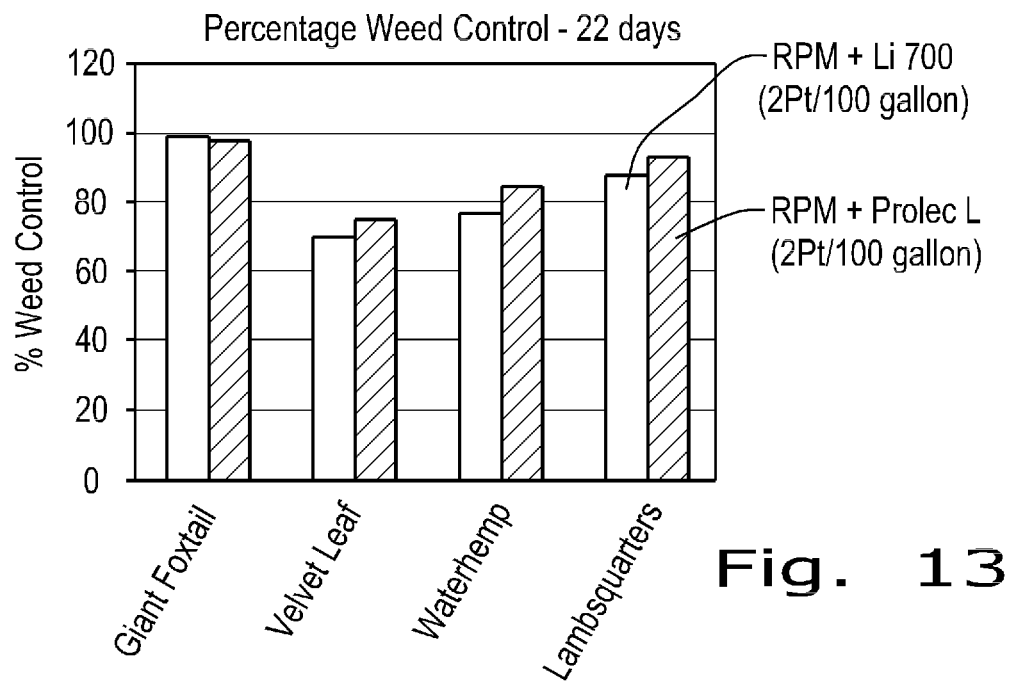
FIG. 13 shows percentage weed control at 22 days of an agricultural adjuvant produced with one embodiment of a microemulsion of the present invention.

In another embodiment, properties of a composition of the present invention referred to as PROLEC L brand agricultural adjuvant were compared to PROLEC G brand agricultural adjuvant (available from Archer-Daniels-Midland Company, Decatur, IL) produced in accordance with US Patent Application Publication 2008/0194410. FIG. 3 shows the surface tension of PROLEC L brand agricultural adjuvant compared to PROLEC G brand agricultural adjuvant and FIG. 4 shows the contact angle of PROLEC L brand agricultural adjuvant compared to PROLEC G brand agricultural adjuvant. FIG. 3 shows that PROLEC L brand agricultural adjuvant of the present invention has more surface tension and a higher contact angle when present at the concentrations of FIG. 3 and FIG. 4, respectively. FIG. 5 shows the pH of PROLEC L brand agricultural adjuvant of the present invention compared to PROLEC G brand agricultural adjuvant at various concentrations.

Table 4 compares data comparing various data points for PROLEC G brand agricultural adjuvant vs. PROLEC L brand agricultural adjuvant. The spray atomization and patternization data was obtained from testing at the Ohio Agricultural Research Developmental Center (OARDC) and it reflects the impact on the coverage, efficiency, and drift. The data presented herein was generated using a Teejet TT11003VS nozzle at 40 psi. The data in this Table refers to the comparison of two different adjuvants containing different acidifiers tested at similar concentration range.

|  | Dv0.5 | | NMD | | % V < 150 | | Av Vel | |
|---|---|---|---|---|---|---|---|---|
|  | PROLEC G | PROLEC L | PROLEC G | PROLEC L | PROLEC G | PROLEC L | PROLEC G | PROLEC L |
| Water | 405.9 | 430.7 | 112.4 | 129.8 | 5.32 | 3.86 | 4.49 | 4.82 |
| RPM | 345.8 | 374.4 | 92.8 | 116.9 | 8.75 | 7.01 | 4.17 | 4.08 |
| RPM + AMS | 341.7 | 375.8 | 92.4 | 120.3 | 9.13 | 6.9 | 4.2 | 4.11 |
| RPM + Prolec | 343.7 | 369.1 | 115.4 | 117.8 | 6.8 | 6.77 | 4.74 | 4.34 |
| RPM + AMS + Prolec | 338.3 | 375.9 | 115.3 | 115.2 | 7.05 | 6.89 | 4.95 | 4.24 |

Figure 16:
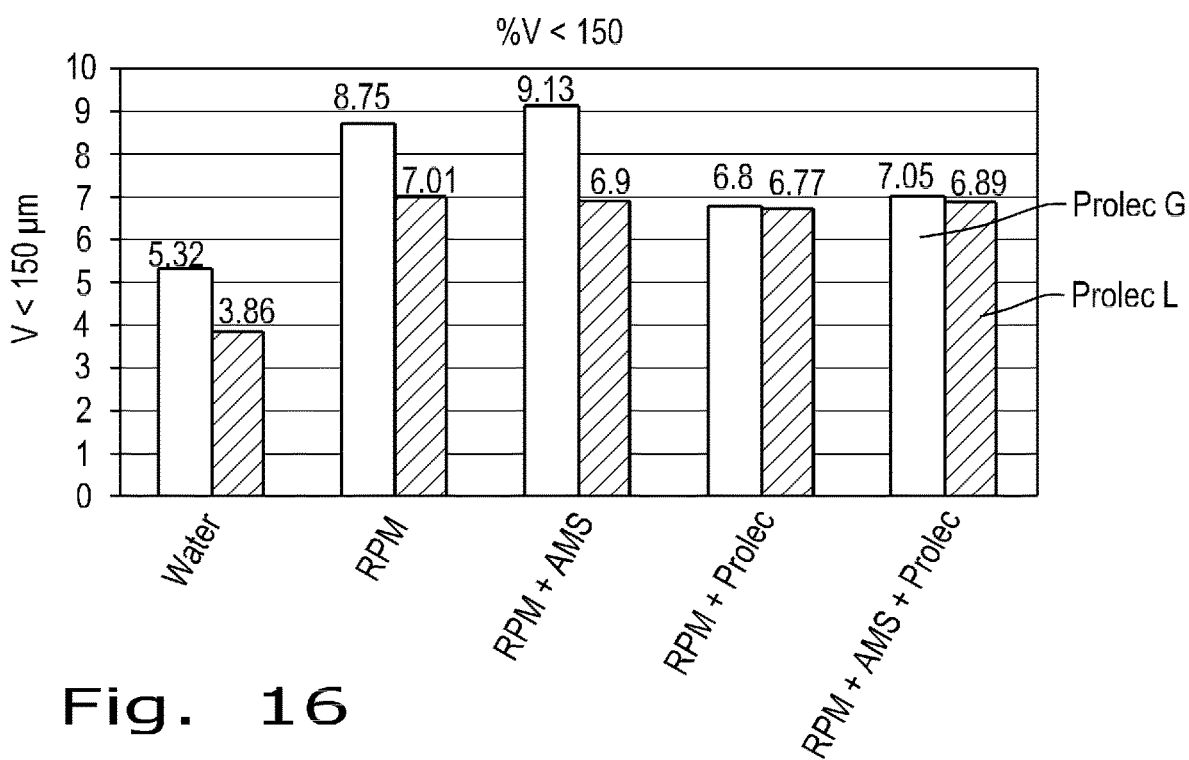
FIG. 16 shows the percentage of volume mean diameter of droplets of an agricultural adjuvant used with an herbicide produced with one embodiment of a microemulsion of the present invention.
Figure 17:
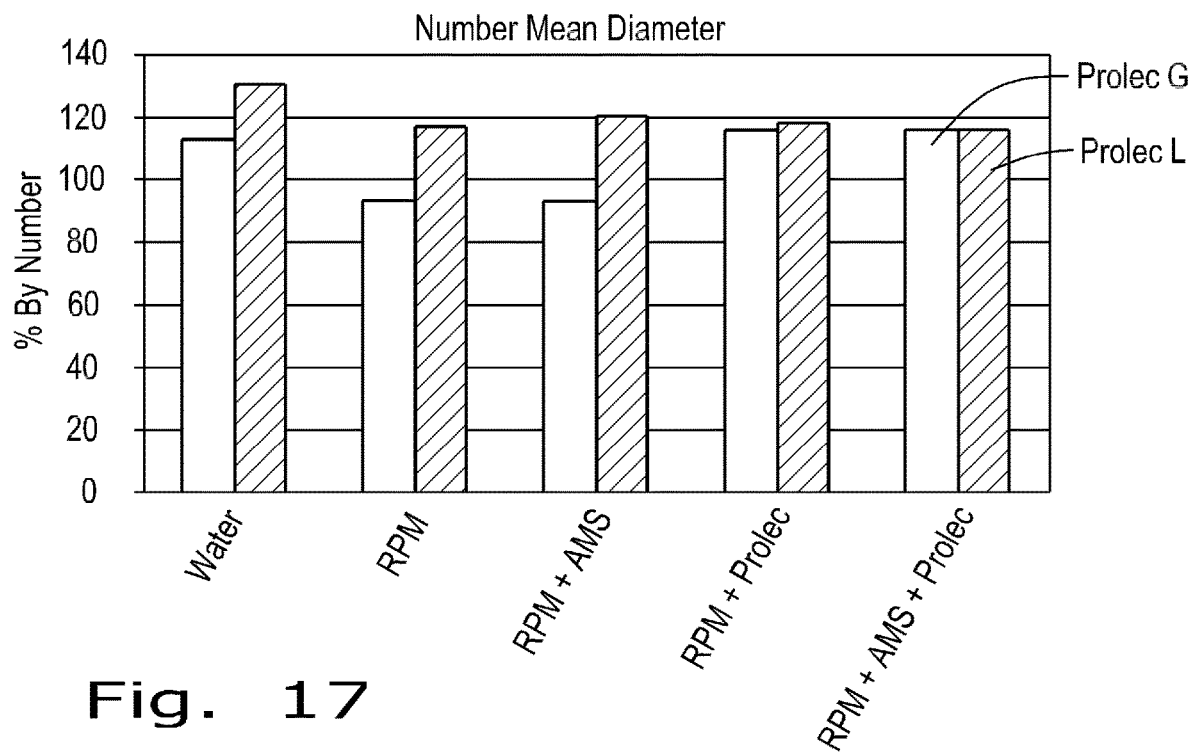
FIG. 17 shows the number mean diameter of droplets of an agricultural adjuvant used with an herbicide produced with one embodiment of a microemulsion of the present invention.

The volume mean diameter for droplets of 150 microns or less was lower than for PROLEC L brand agricultural adjuvant as compared to PROLEC G brand agricultural adjuvant for both water and Round Up as shown in FIG. 16. Similarly, the number mean diameter (droplet size below which 50% of the number of droplets are contained) measured for PROLEC G brand agricultural adjuvant vs PROLEC L brand agricultural adjuvant shows statistically similar results as shown in FIG. 17.

Figure 18:
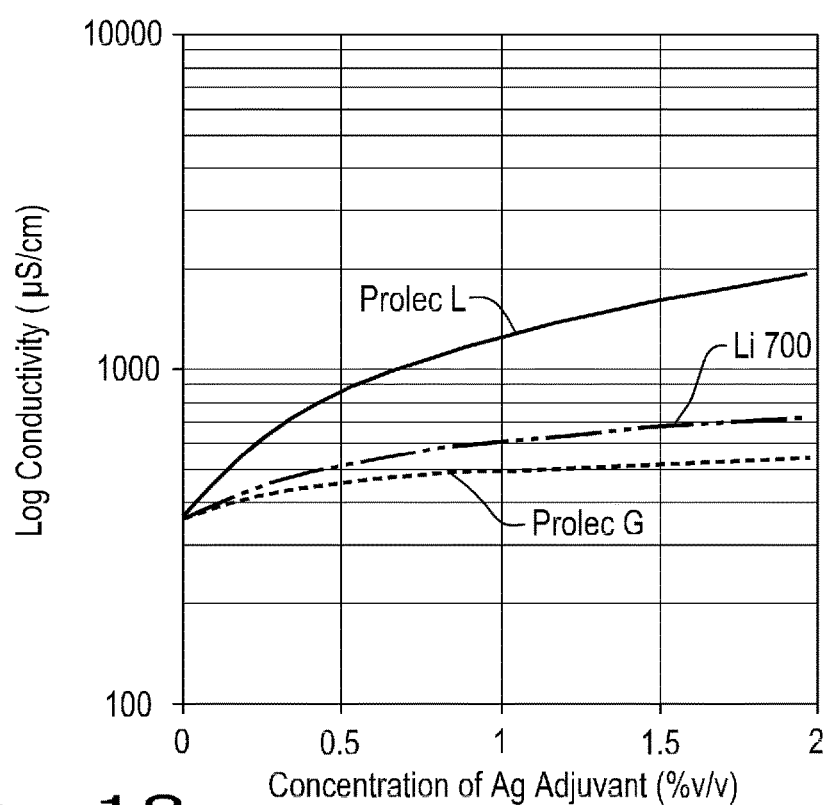
FIG. 18 shows the conductivity of an agricultural adjuvant produced with one embodiment of a microemulsion of the present invention.

Higher conductivity in PROLEC G brand agricultural adjuvant basically shows higher stability in the system in delivering the hydronium ions. Although the concentration of propionic acid is about 35% in PROLEC G brand agricultural adjuvant and Li 700, the mobility of the ions in the solution is going to be very limited. This is because the oil droplets coalesces and affects the ionization effect of the active acid in solution. FIG. 18 shows the conductivity for PROLEC L brand agricultural adjuvant (top line), Li 700 (middle line), and PROLEC G brand agricultural adjuvant (bottom line).

Figure 19:
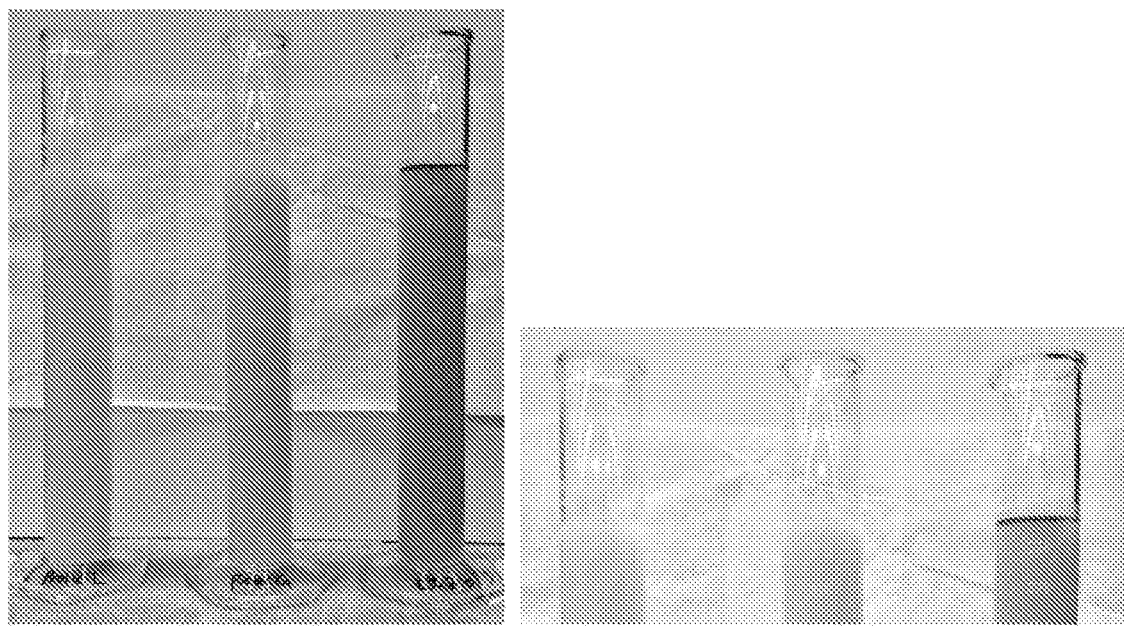
FIG. 19 shows the stability of an agricultural adjuvant produced with one embodiment of a microemulsion of the present invention.

As seen in FIG. 19, Li 700 showed poor stability overnight followed by PROLEC G brand agricultural adjuvant, but with no oil separation. Li 700 and PROLEC G brand agricultural adjuvant are propionic acid based products. PROLEC L brand agricultural adjuvant did not show any separation even after a week dispersed in water. For PROLEC L brand agricultural adjuvant (a lactic based adjuvant), as the concentration of lactic acid is increased, a good increase in the conductivity is increased which shows a stronger electrostatic environment that will offer stability with pH and electrolytes.

Figure 14:
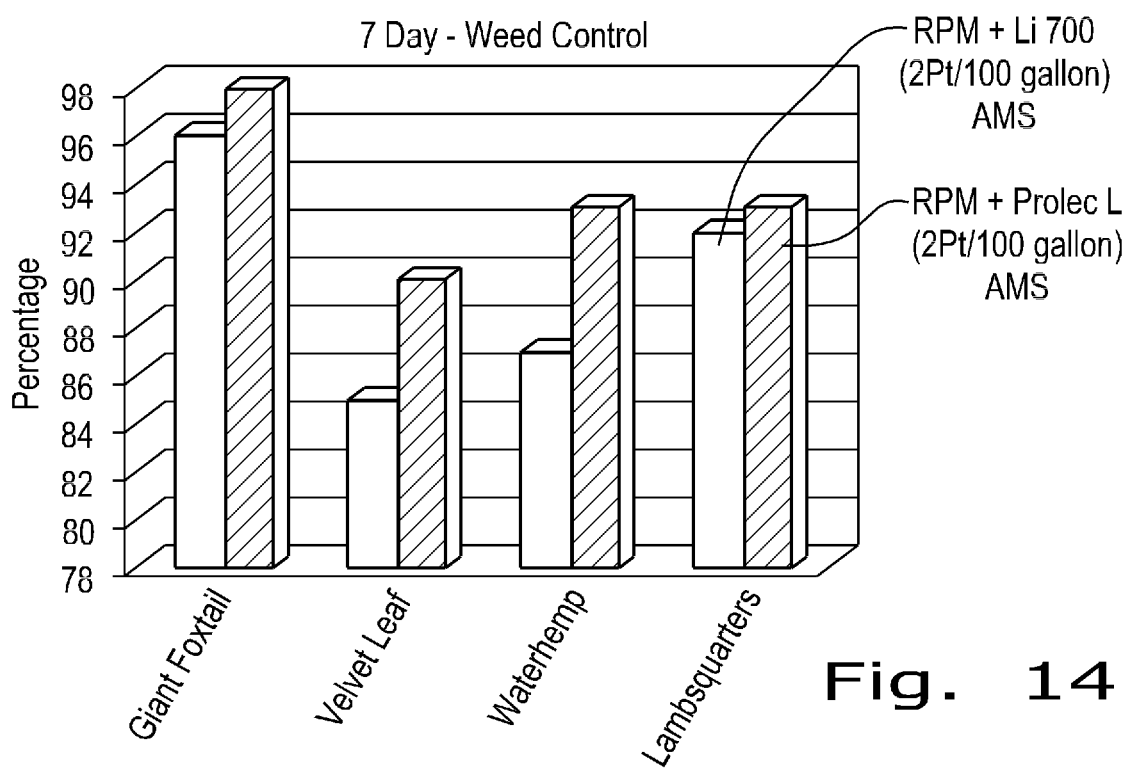
FIG. 14 shows percentage weed control at 7 days of an agricultural adjuvant produced with one embodiment of a microemulsion of the present invention.
Figure 15:
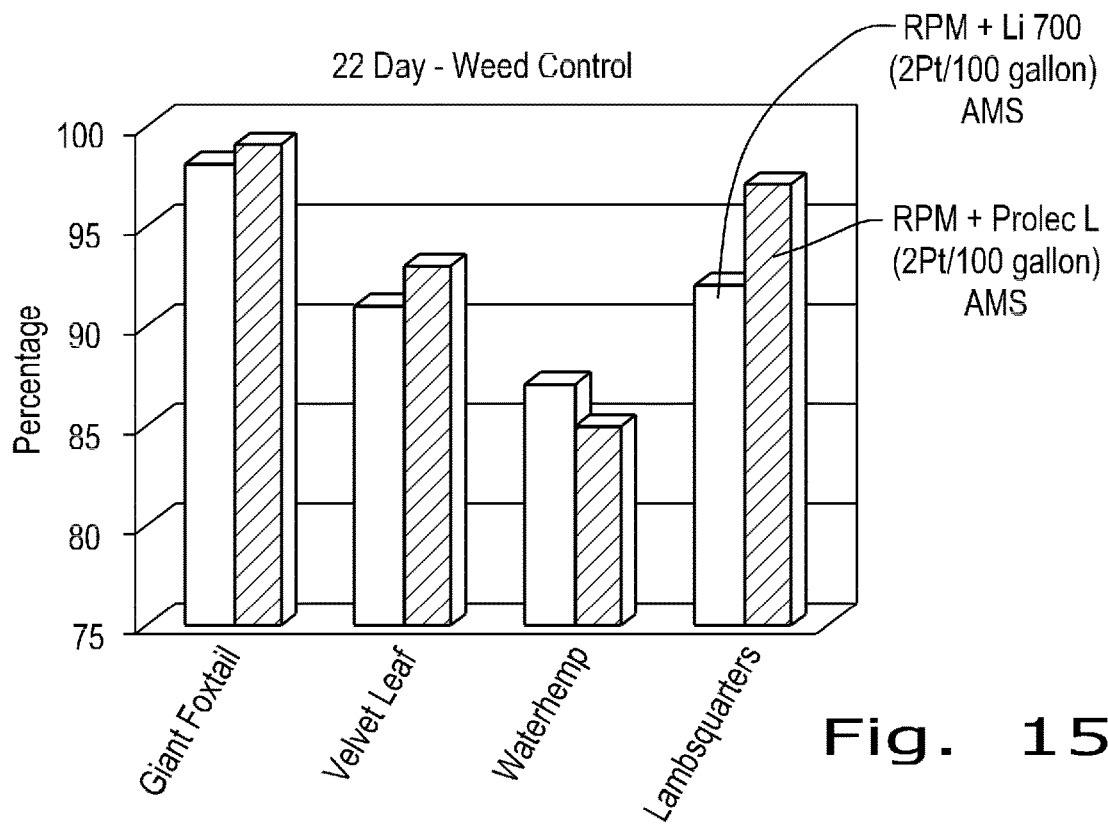
FIG. 15 shows percentage weed control at 22 days of an agricultural adjuvant produced with one embodiment of a microemulsion of the present invention.

The larger the value of $pK_a$, the smaller the extent of dissociation. Propionic acid has a pKa=4.86 which is a relatively weak acid compared to lactic acid with a pKa=3.87. To have the property as an acidifier, an acid that can more readily disassociate in solution, At the same time maintains its effect in a self-assembled system is desired.

Example 22

This example describes one embodiment of a method of making an adjuvant formulation. An adjuvant blend was prepared by mixing a lecithin/high HLB (HLB of 10-18) co-surfactant blend in an amount of 62% by weight; sodium lactate in an amount of 24% by weight; lactic acid in an amount of 9.0% by weight; and ethyl lactate in an amount of 5.0% by weight.

The ingredients were mixed and heated under constant stirring. A stable microemulsion was obtained that may be used as an agricultural adjuvant.

This microemulsion is very hydrophilic and can easily be dispersed in water, especially when the HLB is adjusted to around 10-12. This microemulsion also has a pH of between 4-5.

Example 23

This Example deals with spray atomization and patternization data of microemulsions of the present invention and their impact on coverage, efficiency, and drift. The data presented herein was generated using a Teejet TT11003VS nozzle at 40 psi. The following spray applications were evaluated: 1) water (control); 2) RoundUp PowerMax; 3) RoundUp PowerMax plus Li 700 (2-4 pints/100 gallons); 4) RoundUp PowerMax plus Li 700 (2-4 pints/100 gallons) plus AMS; 5) RoundUp PowerMax plus PROLEC L brand agricultural adjuvant of the present invention (2-8 pints/100 gallons); and 6) RoundUp PowerMax plus PROLEC L brand agricultural adjuvant of the present invention (2-8 pints/100 gallons) plus AMS. Li 700 is a soy-oil derived, non-ionic penetrating surfactant including soy oil, propionic acid, and various surfactants available from Loveland Products Inc., Loveland, CO AMS is a deposition aid/antifoam agent comprising ammonium sulfate, carbamide, poloxanlene, poloxalene, 2-hydroxy-1,2,3-propanetricarboxylic acid, polyacrylamide polymer, and dimethylsiloxane.

This Example includes data sets including Volume Median Diameter (VDM), Number Median Diameter (NMD), distribution of droplets diameter by percent volume and percent number, average velocity, span, etc. FIGS. 6 and 7 are illustrations indicating the difference between VDM and NMD.

The diameter of a droplet can have an effect on drift potential, canopy penetration, surface coverage, and overall efficiency. In general, extremely small droplets that are under 50 microns in diameter remain suspended in the air indefinitely or until they evaporate. Such small droplets should be avoided because, there is no way to control the deposition of these small droplets. Droplet sizes subject to potential drift depends on wind speed and weather conditions, but droplets that are highly, susceptible to drift are generally less than 150 microns. Most pesticide applications should attain a balance between drift reduction provided by large droplets and good coverage provided by small droplets. Spray-droplet size should be no finer than necessary to do an effective job. Recommended droplet sizes for herbicides are approximately 150 to 300 microns for best coverage and efficiency, and between 250-400 microns where drift is of major concern. Studies done with foliar herbicides suggest that droplet sizes in the range of 100 to 400 microns do not significantly differ in weed control, unless application volumes are extremely high or very low. Exceptions to this guideline may exist for specific herbicides, but droplet sizes over 400 microns significantly reduce coverage, retention, and efficiency.

The results of this Example indicate that the PROLEC L brand agricultural adjuvant (the microemulsions of the present invention) reduces the number of fine droplets when compared to water and RoundUp Power Max, and are very similar to commercially available adjuvant Li 700. This Example illustrates that a totally biobased system is viable to replace the propionic acid based commercially available products.

Another advantage of the lactic acid based microemulsion of this example is in the dermal toxicity where propionic acid has a LD 50 value of 500 mg/Kg, while lactic acid has a LD 50 value of greater than 3000 mg/Kg. This creates much safer handling based on the dermal toxicity of the adjuvant systems.

Further, test results shown in FIGS. 6-11 indicate that % droplets by volume of RoundUp PowerMax compared to RoundUp PowerMAX with PROLEC L brand agricultural adjuvant and Li 700 decreased droplets <150 microns as well as decreased the amount of droplet <100 microns as shown in FIG. 6. The data further indicates that PROLEC L brand agricultural adjuvant at a rate of 4 Pints/100 gallons will have a positive effect spray droplet size, and the same drift control as the AMS/polyacrylamide solutions. The PROLEC L brand agricultural adjuvant shows that 8 Pint/100 gallon has a higher droplet percentage at 200-300 micron both in presence and absence of AMS. The results of this Example illustrate that the lactic acid based microemulsions should provide good coverage of the leaf, good penetration in a canopy, good efficiency, and good adhesion and retention when applied in combination with a herbicide, and the lactic acid based microemulsions function as well as, if not better than, other commercially available adjuvants.

Example 24

This Example evaluated the postemergence (on soybean) weed control effect using commercially adjuvant systems and the microemulsions of the present invention applied at various rates of tank-mix partners for crop phytotoxicity and weed efficacy.

This Example determined whether the lecithin adjuvant blend of the present invention was an effective adjuvant for enhancing the performance of glyphosate. To ensure statistical significance, this Example utilized randomized complete block testing and was performed in 3 replications with plot sizes of 10×25 feet. As anticipated, results of the Example indicated that the lecithin adjuvant blend of the present invention applied with glyphosate provided very good weed control indicating weed kill for foxtail, velvet leaf, common waterhemp, and common ragweed to be 99%, 99%, 97%, and 99%, respectively after 21 days. The Example also demonstrated that the lecithin adjuvant blend of the present invention was very safe for soybeans, wherein the percent phytotoxicity was measured to be 5% and 1.7% after 7 and 14 days after application, and further measured to be 0% at 21 days and 28 days after application, respectively. Results of the treatments are shown in FIGS. 12-15. A higher efficiency in weed control was shown at 7 days treatment as well as 22 days when comparing PROLEC L brand agricultural adjuvant of the present invention to the commercially available product Li 700. FIGS. 14 and 15 show almost complete control of the weeds when PROLEC L brand agricultural adjuvant was used in combination with AMS in as early as 7 days with no phototoxicity.

The results of this Example indicate that the PROLEC L brand agricultural adjuvant offers higher penetration and efficacy in the weed control ability with no contribution to phytotoxicity. The results also show the stability of PROLEC L brand agricultural adjuvant even at higher AMS showing stability to higher electrolyte content without compromising on the weed control effect.

This disclosure has been described with reference to certain exemplary embodiments, compositions and uses thereof. However, it will be recognized by those of ordinary skill in the art that various substitutions, modifications or combinations of any of the exemplary embodiments may be made without departing from the spirit and scope of the disclosure. Thus, the disclosure is not limited by the description of the exemplary embodiments, but rather by the appended claims as originally filed.

What is claimed is:

1. A method of dispersing a pesticide in water, the method comprising:
   mixing lecithin and a co-surfactant, thus producing a lecithin concentrate;
   mixing the lecithin concentrate with an acidifier selected from the group consisting of lactic acid, propionic acid, methyl acetic acid, acetic acid, fumaric acid, citric acid, ascorbic acid, gluconic acid, gluconic delta lactone acid, adipic acid, gluconic acid, malic acid, tartaric acid, a hydroxyl acid, and combinations of any thereof, a salt of the acidifier, and an ester of the acidifier, thus forming a microemulsion;
   wherein the microemulsion comprises 5-50% by weight of the acidifier and 5-50% by weight of the salt of the acidifier;
   wherein the microemulsion has a pH of from 2-8;
   mixing the pesticide with the microemulsion; and
   diluting the pesticide and the microemulsion in water, thus dispersing the pesticide in the water.

2. The method according to claim 1, wherein the acidifier is the lactic acid and the salt of the acidifier is a salt of the lactic acid.

3. The method according to claim 1, wherein the microemulsion further comprises fatty acids.

4. The method according to claim 3, wherein the microemulsion further comprises a polar solvent.

5. The method according to claim 4, wherein the microemulsion further comprises a methyl ester.

6. The method according to claim 1, wherein the microemulsion comprises 5-80% by weight of the lecithin and 5-50% by weight of the co-surfactant.

7. The method according to claim 1, wherein the lecithin is fluid lecithin.

8. The method according to claim 1, wherein the co-surfactant has an HLB value of from 10-18.

9. The method according to claim 1, wherein the lecithin is selected from the group consisting of crude filtered lecithin, de-oiled lecithin, chemically modified lecithin, enzymatically modified lecithin, standardized lecithin, and combinations of any thereof.

10. The method according to claim 1, wherein the water is hard water.

11. The method of claim 2, wherein the salt of the lactic acid is sodium lactate and the ester of the acidifier is ethyl lactate.

* * * * *